United States Patent
Keller et al.

(10) Patent No.: US 11,382,587 B2
(45) Date of Patent: Jul. 12, 2022

(54) TECHNIQUES FOR PATIENT POSITIONING QUALITY ASSURANCE PRIOR TO MAMMOGRAPHIC IMAGE ACQUISITION

(71) Applicant: HOLOGIC, INC., Marlborough, MA (US)

(72) Inventors: Brad Michael Keller, Middletown, DE (US); Zhenxue Jing, Chadds Ford, PA (US)

(73) Assignee: Hologic, Inc., Marlborough, MA (US)

( * ) Notice: Subject to any disclaimer, the term of this patent is extended or adjusted under 35 U.S.C. 154(b) by 163 days.

(21) Appl. No.: 16/494,171

(22) PCT Filed: Mar. 15, 2018

(86) PCT No.: PCT/US2018/022635
§ 371 (c)(1),
(2) Date: Sep. 13, 2019

(87) PCT Pub. No.: WO2018/170265
PCT Pub. Date: Sep. 20, 2018

(65) Prior Publication Data
US 2020/0069273 A1    Mar. 5, 2020

Related U.S. Application Data

(60) Provisional application No. 62/471,667, filed on Mar. 15, 2017.

(51) Int. Cl.
*A61B 6/00* (2006.01)
*A61B 6/04* (2006.01)
*A61B 6/02* (2006.01)

(52) U.S. Cl.
CPC ............ *A61B 6/502* (2013.01); *A61B 6/04* (2013.01); *A61B 6/488* (2013.01); *A61B 6/542* (2013.01); *A61B 6/545* (2013.01); *A61B 6/025* (2013.01)

(58) Field of Classification Search
CPC .......... A61B 6/025; A61B 6/04; A61B 6/488; A61B 6/502; A61B 6/542; A61B 6/544; A61B 6/545; A61B 6/54
(Continued)

(56) References Cited

U.S. PATENT DOCUMENTS 7,582,860 B2 * 9/2009 Kusunoki ............... A61B 6/583
250/252.1
7,613,276 B2 * 11/2009 Sendai ................. A61B 6/0414
378/37
(Continued)

FOREIGN PATENT DOCUMENTS

EP     2428163 A2    3/2012

OTHER PUBLICATIONS

International Search Report and Written Opinion for International application No. PCT/US2018/022635, dated Jun. 15, 2018, 11 pages.
(Continued)

*Primary Examiner* — Allen C. Ho
(74) *Attorney, Agent, or Firm* — Merchant & Gould P.C.

(57) ABSTRACT

Techniques for patient positioning quality assurance prior to mammographic image acquisition are described. A system may include an x-ray source configured to expose human tissue to radiation. An x-ray detector module may be configured to detect the radiation and generate a pre-diagnostic image of the human tissue. A position analysis module may be configured to receive the pre-diagnostic image and determine whether the human tissue is positioned correctly based upon one or more predefined positioning criteria. A non-transitory computer-readable storage medium may be configured to store the results of the positional analysis module determination. A display may be configured to display the
(Continued)

determination of the position analysis module within a user interface. Other embodiments are described and claimed.

18 Claims, 17 Drawing Sheets

(58) Field of Classification Search
USPC .................. 378/22, 25, 37, 62, 196, 197, 26
See application file for complete search history.

(56) References Cited

U.S. PATENT DOCUMENTS

| | | | | |
|---|---|---|---|---|
| 7,792,243 B2* | 9/2010 | Strommer | ............ | A61B 6/4233 |
| | | | | 378/37 |
| 8,051,386 B2* | 11/2011 | Rosander | ............... | G16H 50/20 |
| | | | | 715/810 |
| 8,288,729 B2* | 10/2012 | Ogawa | ..................... | G01T 1/247 |
| | | | | 250/370.08 |
| 8,326,012 B2* | 12/2012 | Kreeger | ................. | G06T 11/60 |
| | | | | 382/132 |
| 8,391,572 B2* | 3/2013 | Morita | ................. | A61B 6/5217 |
| | | | | 382/128 |
| 8,571,174 B2* | 10/2013 | Smith | .................... | A61B 6/025 |
| | | | | 378/37 |
| 8,744,041 B2* | 6/2014 | Smith | .................. | A61B 6/5211 |
| | | | | 378/37 |
| 8,874,187 B2* | 10/2014 | Thomson | ............. | A61N 5/1049 |
| | | | | 600/407 |
| 9,117,315 B2* | 8/2015 | Tajima | ................... | A61B 6/502 |
| 9,129,362 B2* | 9/2015 | Jerebko | ................. | A61B 6/502 |
| 9,168,013 B2* | 10/2015 | Roessl | ................... | A61B 6/488 |
| 10,092,264 B2* | 10/2018 | Machida | ............. | A61B 6/5235 |
| 10,102,622 B2* | 10/2018 | Ishikawa | ................... | G06T 7/13 |
| 10,335,107 B2* | 7/2019 | Fukuda | ................ | A61B 6/5205 |
| 10,433,795 B2* | 10/2019 | Nakayama | ............. | A61B 6/502 |
| 10,463,328 B2* | 11/2019 | Tsukagoshi | ............ | A61B 6/469 |
| 10,540,764 B2* | 1/2020 | Tsukagoshi | ............ | A61B 6/032 |
| 2010/0104166 A1 | 4/2010 | Hall et al. | | |
| 2013/0251104 A1 | 9/2013 | Roessl et al. | | |

OTHER PUBLICATIONS

PCT International Preliminary Report on Patentability in Application PCT/US2018/022635, dated Sep. 26, 2019, 9 pages.

* cited by examiner

CC View
210

MLO View
200

Nipple not in profile

900

902

Combined CC view shows pectoralis in middle

TECHNIQUES FOR PATIENT POSITIONING QUALITY ASSURANCE PRIOR TO MAMMOGRAPHIC IMAGE ACQUISITION

CROSS-REFERENCE TO RELATED APPLICATIONS

This application is a National Stage Application of PCT/US2018/022635, filed Mar. 15, 2018, which claims the benefit of U.S. Provisional Application No. 62/471,667, filed Mar. 15, 2017, which are incorporated herein by reference in their entireties. To the extent appropriate, a claim of priority is made to each of the above disclosed applications.

FIELD OF THE DISCLOSURE

Embodiments described herein generally relate to quality assurance of patient positioning, and more particularly, to improving patient positioning in breast imaging, such as it relates to mammographic or tomosynthesis image acquisition.

BACKGROUND

Proper positioning is important when performing radiation-based imaging of a patient for a variety of reasons. First, the position of the target tissue is crucial to obtain a quality image that can be used for diagnosis. Second, it is desirable to minimize a patient's total exposure to radiation during a study and, thus, subsequent imaging to obtain proper positioning is not ideal. Third, due to regulations in many jurisdictions, subsequent imaging used solely to correct poor positioning may be counted against a practitioner or organization, and frequent re-imaging may result in revocation of a license and/or accreditation. Fourth, improper positioning for an image may require a patient to make subsequent visits to an imaging center, placing additional burden on the patient. For at least these reasons, there is a need for improved techniques, which may be automated or semi-automated, for quality assurance in patient positioning, for assessing prior information longitudinally across a patient record, and for minimizing the amount of radiation exposure to patients in a workflow efficient manner.

SUMMARY

The following presents a simplified summary in order to provide a basic understanding of some novel embodiments described herein. This summary is not an extensive overview, and it is not intended to identify key/critical elements or to delineate the scope thereof. Its sole purpose is to present some concepts in a simplified form as a prelude to the more detailed description that is presented later.

Techniques for patient positioning quality assurance prior to image acquisition are described. In an embodiment, a system may include an x-ray source configured to expose human tissue to radiation. In some embodiments, the human tissue may include breast tissue. An x-ray detector may be configured to detect the radiation and generate a pre-diagnostic image of the human tissue. As used herein, a pre-diagnostic image is one in which (a) a relatively low amount of radiation exposure to the tissue is utilized (a "pre-diagnostic dose level") and analyzed in order to determine the optimal exposure parameters to generate a diagnostic quality image, such as could be, but not necessarily, generated by the automated exposure control system of a breast imaging system; and (b) is not intended to be presented for clinical or diagnostic interpretation by a physician or other healthcare provider or staff. A position analysis module may be configured to receive the pre-diagnostic image and determine whether the human tissue is positioned correctly based upon one or more predefined positioning criteria. A non-transitory computer-readable storage medium may be configured to store the results of the positional analysis module determination. A display may be configured to display the determination of the position analysis module within a user interface. Other embodiments are described and claimed.

In an embodiment, an imaging system may include an x-ray source to expose human tissue to radiation at pre-diagnostic dose levels, an x-ray detector to detect the radiation and generate a pre-diagnostic image of the human tissue, and a position analysis module to receive the pre-diagnostic image and determine whether the human tissue is positioned correctly based upon one or more predefined positioning criteria.

In an embodiment, a computer-implemented method may include exposing human tissue to radiation by an x-ray source, an x-ray detector module configured to detect the radiation and generate a pre-diagnostic image of the human tissue, receiving the pre-diagnostic image at a position analysis module, and determining, by the position analysis module, whether the human tissue is positioned correctly based upon one or more predefined positioning criteria. In some embodiments, In some embodiments, the human tissue is a breast and the imaging system is operative to capture a diagnostic mammogram of the breast. In various embodiments, a radiation level used to generate the pre-diagnostic image is substantially less than a radiation level to generate a diagnostic image. In some embodiments, the pre-diagnostic image is of a lower resolution than a diagnostic image. In exemplary embodiments, the pre-diagnostic image is an automated exposure control (AEC) scout image. In some embodiments, the pre-diagnostic image is of a mediolateral oblique (MLO) view of a breast. In various embodiments, the pre-diagnostic image is of a cranial-caudal (CC) view of a breast. In exemplary embodiments, the predefined criteria are compared to one or more detected anatomical landmarks. In various embodiments, the one or more detected anatomical landmarks are selected from the group comprising an inframammary fold, nipple, pectoral muscles, or chest wall. In some embodiments, the predefined criteria include a comparison between the pre-diagnostic image and one or more of previous pre-diagnostic images or previous diagnostic images. In some embodiments, the imaging system may include a display configured to display the determination of the position analysis module within a user interface. In various embodiments, the pre-diagnostic image is of a substantially similar resolution to a diagnostic image. In some embodiments, a diagnostic image is automatically taken based upon the determination of the position analysis module. In various embodiments, a diagnostic image procedure is automatically interrupted based upon the determination of the position analysis module. In some embodiments, a diagnostic image procedure is interrupted in response to receiving a user input based upon the determination of the position analysis module.

To the accomplishment of the foregoing and related ends, certain illustrative aspects are described herein in connection with the following description and the annexed drawings. These aspects are indicative of the various ways in which the principles disclosed herein can be practiced and all aspects and equivalents thereof are intended to be within the scope of the claimed subject matter. Other advantages and novel features will become apparent from the following detailed description when considered in conjunction with the drawings.

DETAILED DESCRIPTION

Figure 12B:
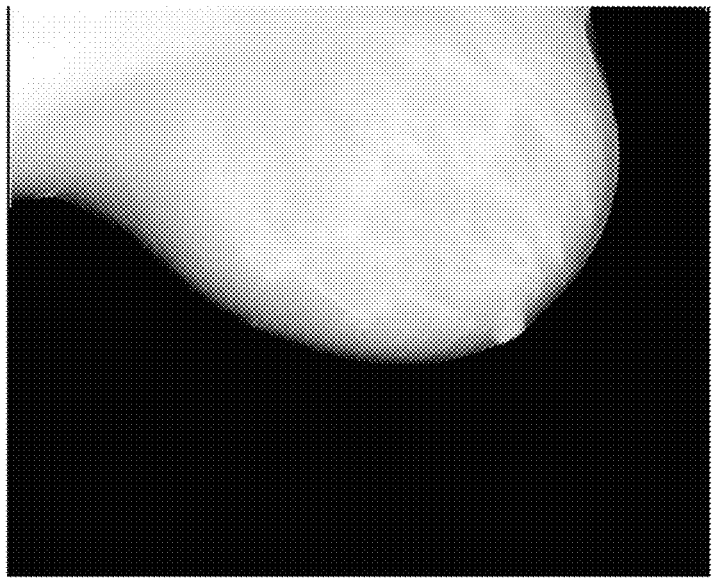
FIG. 12B illustrates an exemplary pre-diagnostic image.
Figure 12A:
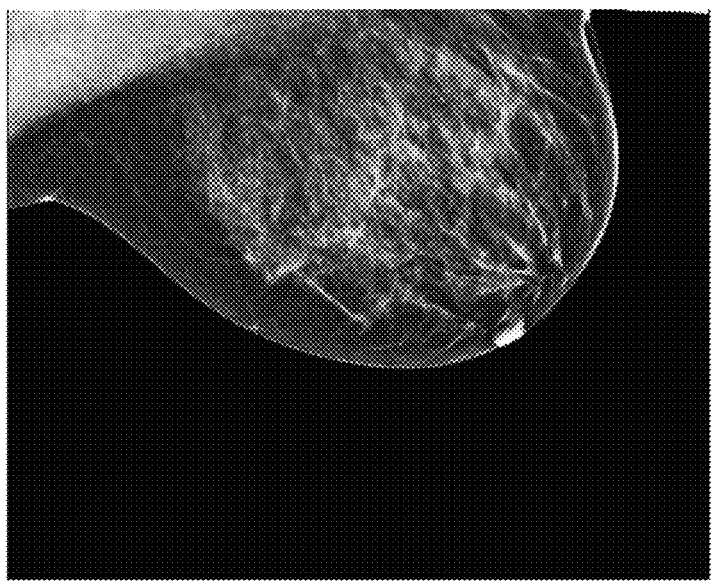
FIG. 12A illustrates an exemplary diagnostic image.

Various embodiments are generally directed to techniques for patient positioning quality assurance prior to mammographic image acquisition are described. In an embodiment, a system may include an x-ray source configured to expose human tissue to radiation. An x-ray detector may be configured to detect the radiation and generate a pre-diagnostic image of the human tissue. As used herein, a pre-diagnostic image is one in which (a) a relatively low amount of radiation exposure to the tissue is utilized and analyzed in order to determine the optimal exposure parameters to generate a diagnostic quality image, such as could be, but not necessarily, generated by the automated exposure control system of a breast imaging system; and (b) is not intended to be presented for clinical or diagnostic interpretation by a physician or other healthcare provider or staff. An exemplary comparison between a diagnostic image and a pre-diagnostic image is illustrated by FIGS. 12A and 12B. A position analysis module may be configured to receive the pre-diagnostic image and determine whether the human tissue is positioned correctly based upon one or more predefined positioning criteria. A non-transitory computer-readable storage medium may be configured to store the results of the positional analysis module determination. A display may be configured to display the determination of the position analysis module within a user interface. Other embodiments are described and claimed.

With general reference to notations and nomenclature used herein, the detailed descriptions which follow may be presented in terms of program procedures executed on a computer or network of computers. These procedural descriptions and representations are used by those skilled in the art to most effectively convey the substance of their work to others skilled in the art.

A procedure is here, and generally, conceived to be a self-consistent sequence of operations leading to a desired result. These operations are those requiring physical manipulations of physical quantities. Usually, though not necessarily, these quantities take the form of electrical, magnetic or optical signals capable of being stored, transferred, combined, compared, and otherwise manipulated. It proves convenient at times, principally for reasons of common usage, to refer to these signals as bits, values, elements, symbols, characters, terms, numbers, or the like. It should be noted, however, that all of these and similar terms are to be associated with the appropriate physical quantities and are merely convenient labels applied to those quantities.

Various embodiments also relate to apparatus or systems for performing these operations. In some embodiments, these apparatus may be specially constructed for the required purpose or it may comprise a computing device selectively activated, operated, and/or configured by a computer program stored in the computing device and/or hardware of the computing device. Various machines may be used with programs written and/or hardware configured in accordance with the teachings herein, including specialized apparatus to perform the required method steps. The required structure for a variety of these machines will appear from the description given.

Figure 1:
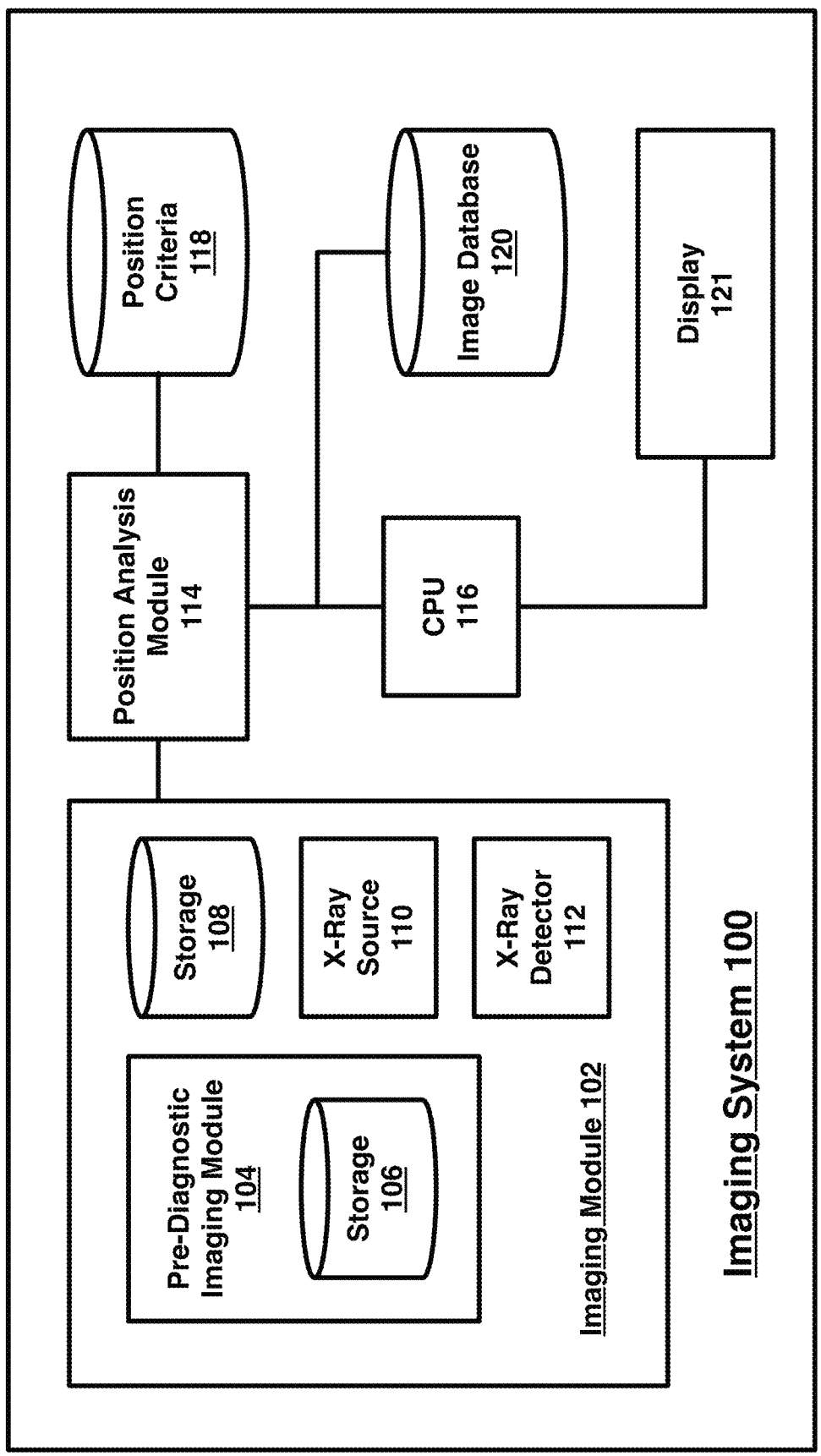
FIG. 1 illustrates an embodiment of a system.

FIG. 1 illustrates a block diagram for an imaging system 100. In one embodiment, the imaging system 100 may comprise one or more components. Although the imaging system 100 shown in FIG. 1 has a limited number of elements in a certain topology, it may be appreciated that the imaging system 100 may include more or less elements in alternate topologies as desired for a given implementation. The imaging system 100 may include a plurality of modules, including imaging module 102, pre-diagnostic imaging module 104, and position analysis module 114, which may each include one or more processing units, storage units, network interfaces, or other hardware and software elements described in more detail herein. In some embodiments, these modules may be included within a single imaging device, utilizing shared CPU 116. In other embodiments, one or more modules may be part of a distributed architecture, an example of which is described with respect to FIG. 15.

In an embodiment, each module of imaging system 100 may comprise without limitation an imaging system, mobile computing device, a smart phone, a desktop computer, or other devices described herein. In various embodiments, imaging system 100 may comprise or implement multiple components or modules. As used herein the terms "component" and "module" are intended to refer to computer-related entities, comprising either hardware, a combination of hardware and software, software, or software in execution. For example, a component and/or module can be implemented as a process running on a processor, such as CPU 116, a hard disk drive, multiple storage drives (of optical and/or magnetic storage medium), an object, an executable, a thread of execution, a program, logic, circuitry, a controller, and/or a computer. By way of illustration, both an application running on a server and the server can be a component and/or module. One or more components and/or modules can reside within a process and/or thread of execution, and a component and/or module can be localized on one computer and/or distributed between two or more computers as desired for a given implementation. The embodiments are not limited in this context.

The various devices within system 100, and components and/or modules within a device of system 100, may be communicatively coupled via various types of communications media as indicated by various lines or arrows. In various embodiments, the various modules and storages of system 100 may be organized as a distributed system. A distributed system typically comprises multiple autonomous computers that communicate through a computer network. It is worthy to note that although some embodiments may utilize a distributed system when describing various enhanced techniques for data retrieval, it may be appreciated that the enhanced techniques for data retrieval may be implemented by a single computing device as well. The embodiments are not limited in this context.

In an embodiment, imaging module 102 may include an x-ray source 110 and x-ray detector 112, which may be used to perform breast imaging. In some embodiments imaging module 102 may be configured to perform breast imaging, such as x-ray mammography and/or tomosynthesis, which is a method for performing high-resolution limited-angle tomography at radiographic dose levels. While mammography is used as an exemplary embodiment through the description, it can be appreciated that the techniques described herein may be applicable to other procedures in which radiation minimization and proper patient positioning is desirable.

X-ray source 110 may be configured to expose human tissue to x-rays, which may be detected by x-ray detector 112. X-ray detector 112 may be configured to respond to the fluence of incident x-rays over a wide range. X-ray detector 112 may be configured to absorb x-rays, produce an electronic signal, digitize the signal, and store the results in one of storage 108 and/or 120. The output image may be saved as a two-dimensional matrix, where each element represents the x-ray transmission corresponding to a path through the breast tissue. Three-dimensional images and matrices may be generated in some embodiments, depending on the imaging modality, such as tomosynthesis, computed tomography, and the like. The image may be digitally processed such that when it is displayed on a display device or printed on laser film, it will illustrate the key features required for diagnosis. Such diagnostic images may be stored in storage 108 so that they may be viewed on a user interface of display 121. In an embodiment, images may also be archived in image database 120. In this manner, patient records may be maintained and past images may be used to evaluate patient positioning when compared to new images.

Imaging system 100 may include pre-diagnostic imaging module 104, which may be configured to generate automated exposure control (AEC) scout images using x-ray source 110 and x-ray detector 112. AEC scout images may be stored in storage 106, which may be a temporary storage used for calibration operations and, in some embodiments, in conjunction with position analysis module 104, discussed below. AEC scout images may be pre-diagnostic, as described herein, and used to measure and calibrate radiation levels within an imaging system prior to taking diagnostic images. In other words, AEC scout images may be taken prior to typical diagnostic images. In some embodiments, AEC scout images may be of a lower resolution than diagnostic images. However, in other examples, AEC scout images may be of similar resolution to diagnostic images. Pre-diagnostic AEC scout images may be acquired using 2-10% of the radiation dose as would a diagnostic image of the same tissue, in some examples. It can be appreciated, however, that pre-diagnostic images may use more or less radiation in particular embodiments, but will typically be less than a diagnostic image. In some embodiments, the AEC scout image may be acquired in a single x-ray exposure; in other embodiments, the AEC scout image may be acquired over multiple x-ray exposures.

Since AEC scout images typically have very low radiation exposure when compared to diagnostic images, it is advantageous to utilize them to perform patient positioning. While the very low radiation dosage of pre-diagnostic images is beneficial to patients during positioning and used to determine necessary x-ray parameters to generate a diagnostic quality image, the low level of radiation exposure used may also lead to significantly decreased quality of the pre-diagnostic image, which is a key reason it is not presented for human interpretation. However, despite the inherent difficulties in analyzing low-quality pre-diagnostic images, advanced image analysis software modules may still be utilized to automatically or semi-automatically process and extract relevant information to assist with proper patient positioning. In an example, pre-diagnostic images may have increased noise and reduced contrast, when compared to diagnostic images. An exemplary comparison between a diagnostic image and a pre-diagnostic image is illustrated by FIGS. 12A and 12B. To mitigate reduced quality of pre-diagnostic images, some embodiments may automatically or semi-automatically decrease the resolution of the pre-diagnostic image, which may inflate a local signal-to-noise ratio of objects and/or anatomy within the pre-diagnostic image.

Imaging system 100 may include position analysis module 114, operative on CPU 116, and configured to identify one or more anatomical landmarks within a pre-diagnostic image. Further, position analysis module 114 may determine whether a patient's position is proper based upon one or more position criteria stored within position criteria repository 118. Criteria for proper positioning may be predefined as set forth by various accrediting bodies, such as the Food and Drug Administration, American College of Radiology, European Commission, and others. Some examples of criteria indicating improper and proper positioning are illustrated below with respect to FIGS. 3-10.

In an embodiment, position analysis module 114 may receive a pre-diagnostic image from pre-diagnostic image module 104. Position analysis module 114 may evaluate the received image, which may be of a lower quality when compared to a diagnostic image. Using algorithms optimized to identify anatomical landmarks within low quality pre-diagnostic images, position analysis module 114 may identify one or more anatomical landmarks as discussed with respect to FIGS. 2A and 2B below. Some pertinent anatomical landmarks that may be used to determine proper positioning include, but are not limited to, the nipple, pectoralis muscle, or other non-targeted anatomical structures being in view such as ears, fingers, stomach, and so on. In an exemplary embodiment, position analysis module 114 may be optimized to detect and identify landmarks of particularly low contrast in pre-diagnostic quality images, such as the nipple or internal structures such as the edge of the pectoralis muscle.

Once identified, characteristics of detected anatomical landmarks (e.g. location, position, presence, size, relationship to other landmarks, etc.) may be compared to one or more predefined criteria from position criteria repository 118. Based upon the comparison, position analysis module 114 may make a position determination. Further, position analysis module 114 may make a position determination based upon the relationship of a first landmark to one or more additional landmarks, and/or a comparison of a current pre-diagnostic view with a previous pre-diagnostic or diagnostic view accessible from image database 120. A position determination may indicate whether a patient is currently in an acceptable position, or needs to be repositioned.

In an embodiment, display device 121 may include a user interface configured to receive and display a determination of patient positioning from position analysis module 114. For example, a practitioner may be notified via the user interface of display 121 that a patient is properly or improperly positioned. Further, position analysis module 114 may indicate to a practitioner, based upon a position determination, suggested movements for a patient to obtain proper positioning prior to a diagnostic image. In addition to a notification via the user interface of display 121, other techniques for notification of improper position may be used. Non-limiting examples include audio notification, haptic notification, visual indication using lights, and/or one or more prompts within the user interface.

In one example, in response to the display 121 notifying the practitioner that the patient is improperly positioned, the practitioner may be provided with an option via the display device 121 to interrupt the imaging module 102 from taking the full exposure diagnostic image. If the practitioner selects the option to interrupt, the input is received via the display device 121 and the imaging module 102 prevents the x-ray source 110 from being activated. The practitioner may then manually reposition the patient and may then repeat or restart the procedure starting with the pre-diagnostic image and another determination of patient positioning. In another example, a determination of patient positioning from a position analysis module 114 that the patient is improperly positioned may be used to automatically interrupt the imaging module 102 from taking the full exposure diagnostic by activating the x-ray source. Similar to above, the practitioner can then reposition the patient and repeat or restart the imaging procedure starting with the pre-diagnostic imaging and position determination. In this manner, unnecessary radiation may be reduced during an imaging study of the patient because full-exposure of the higher dose is interrupted either automatically or manually via the practitioner.

In some embodiments, a determination of patient positioning from a position analysis module 114 may be used to automatically allow a diagnostic image to be taken immediately, substantially immediately, or otherwise within an image timing duration following a determination that a patient is properly positioned. In this manner, once a patient is determined to be properly positioned by position analysis module 114, a diagnostic image may be automatically taken by imaging module 102 quickly thereafter while the patient is in the proper position, minimizing the opportunity for the patient to be placed in an improper position. Likewise, a determination of patient positioning from a position analysis module may be used to automatically terminate a diagnostic image exposure when improper patient positioning is detected. In this manner, unnecessary radiation may be reduced during an imaging study of the patient. The image timing duration may include various time values, including, without limitation, less than 1 second, 1 second, 2 seconds, 5 seconds, 10 seconds, 20 seconds, 30 seconds, 1 minute, 2 minutes, 5 minutes, 10 minutes, and values and ranges between any two of these values (including endpoints).

Figure 2B:
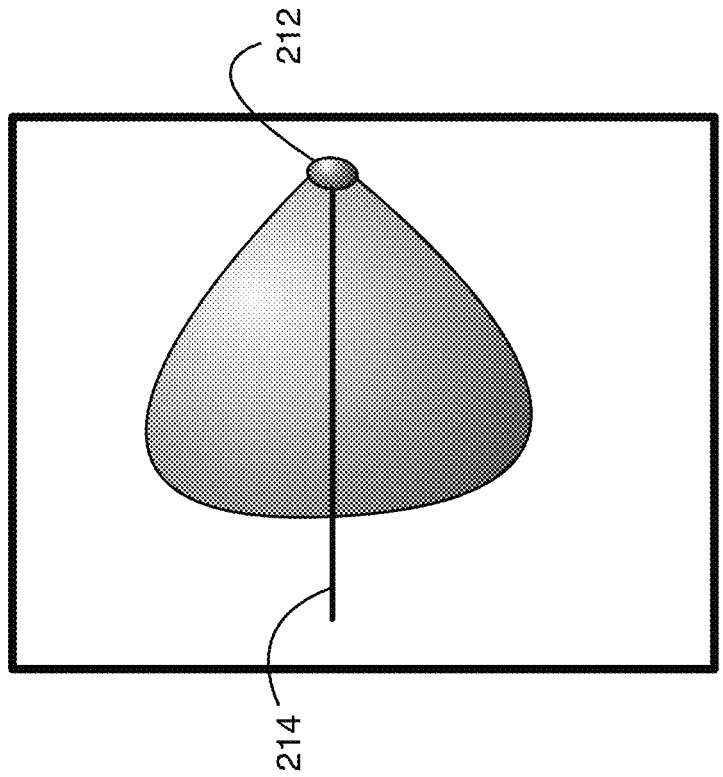
FIG. 2B illustrates a mammography image according to an embodiment.
Figure 2A:
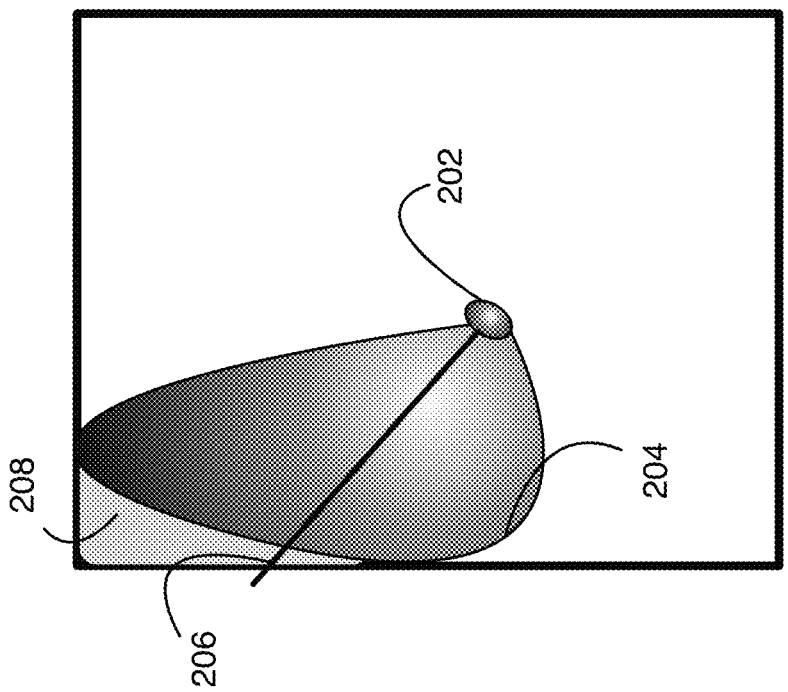
FIG. 2A illustrates a mammography image according to an embodiment.

FIG. 2A illustrates a pre-diagnostic mammography image 200 according to an embodiment. Specifically, pre-diagnostic mammography image 200 illustrates a mediolateral oblique (MLO) view of the breast. As illustrated within FIG. 2A, a series of anatomical landmarks may be identified by a position analysis module to determine whether a patient is properly positioned prior to taking a diagnostic image of the patient's breast. While four landmarks are illustrated within FIG. 2A, it can be appreciated that other landmarks may be used in addition to those illustrated. A position analysis module may compare characteristics (e.g., location, position, presence, size, relationship to other landmarks, etc.) of a particular landmark to one or more predefined criteria and make a position determination based upon a review of one or more landmarks. In some embodiments, a position analysis module may make a position determination based upon the relationship of a first landmark to one or more additional landmarks. In various embodiments, a position analysis module may compare a landmark from a first view to one or more landmarks from additional views, which may be taken from a current or previous study of the patient.

As a first example, nipple 202 may be identified by a position analysis module. In some embodiments, the alignment of nipple 202 may be compared to one or more predefined criteria to determine whether a patient is properly positioned. For example, the absence of a nipple within pre-diagnostic mammography image 200 may indicate to a position analysis module that a patient is improperly positioned.

As a second example, inframammary fold 204 may be identified by a position analysis module. Inframammary fold 204 may represent the anatomical boundary formed at the inferior border of the breast, where it joins with the chest. The presence of inframammary fold 204 may provide evidence that a patient is properly positioned, while absence of inframammary fold 204 within pre-diagnostic mammography image 200 may indicate that the patient is improperly positioned.

As a third example, posterior nipple line (PNL) 206 may be identified by a position analysis module. PNL 206 may represent a line drawn posteriorly and perpendicularly from the nipple towards the pectoral muscle on the mammogram. In some embodiments, a comparison may be made between this line on different views (MLO, CC) to determine whether positioning of a patient is satisfactory. As one example, in an adequately exposed breast, the difference between a measurement of the PNL line may be within approximately 1 cm between views, or between breasts of the same view.

In a fourth example, pectoralis muscle 208 may be identified by a position analysis module. Pectoralis muscle 208 may be especially pronounced in MLO views and may be analyzed to determine whether a sufficient amount of breast tissue is depicted within the pre-diagnostic mammography image 200 to make a diagnosis. Insufficient breast tissue coverage may indicate improper positioning of a patient.

FIG. 2B illustrates a pre-diagnostic mammography image 210 according to an embodiment. Specifically, pre-diagnostic mammography image 210 illustrates a cranial-caudal (CC) view of the breast. Like with MLO view, one or more anatomical landmarks, such as nipple 212 and PNL 214 may be identified by a position analysis module. A position analysis module may compare characteristics (e.g. location, position, presence, size, relationship to other landmarks, etc.) of a particular landmark to one or more predefined criteria and make a position determination based upon a review of one or more landmarks. In various embodiments, a position analysis module may make a position determination based upon the relationship of a first landmark to one or more additional landmarks. In exemplary embodiments, a position analysis module may compare a landmark from a first view to one or more landmarks from additional views, which may be taken from a current or previous study of the patient.

Figure 3:
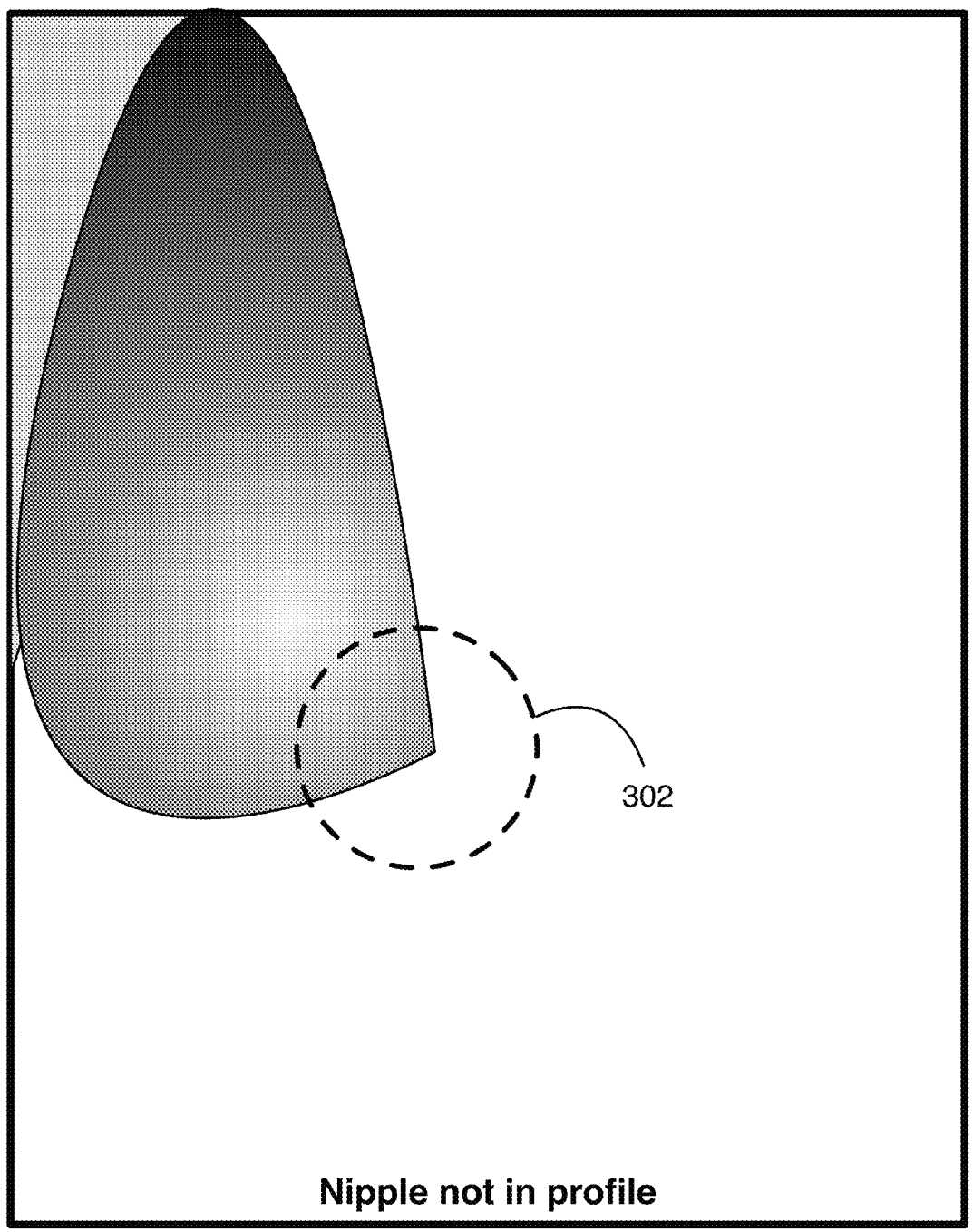
FIG. 3 illustrates a mammography image according to an embodiment.

FIG. 3 illustrates a pre-diagnostic mammography image 300 according to an embodiment. As illustrated within pre-diagnostic mammography image 300, a position analysis module may identify region 302 as lacking a nipple within a profile of the breast, which may indicate improper positioning of a patient.

Figure 4:
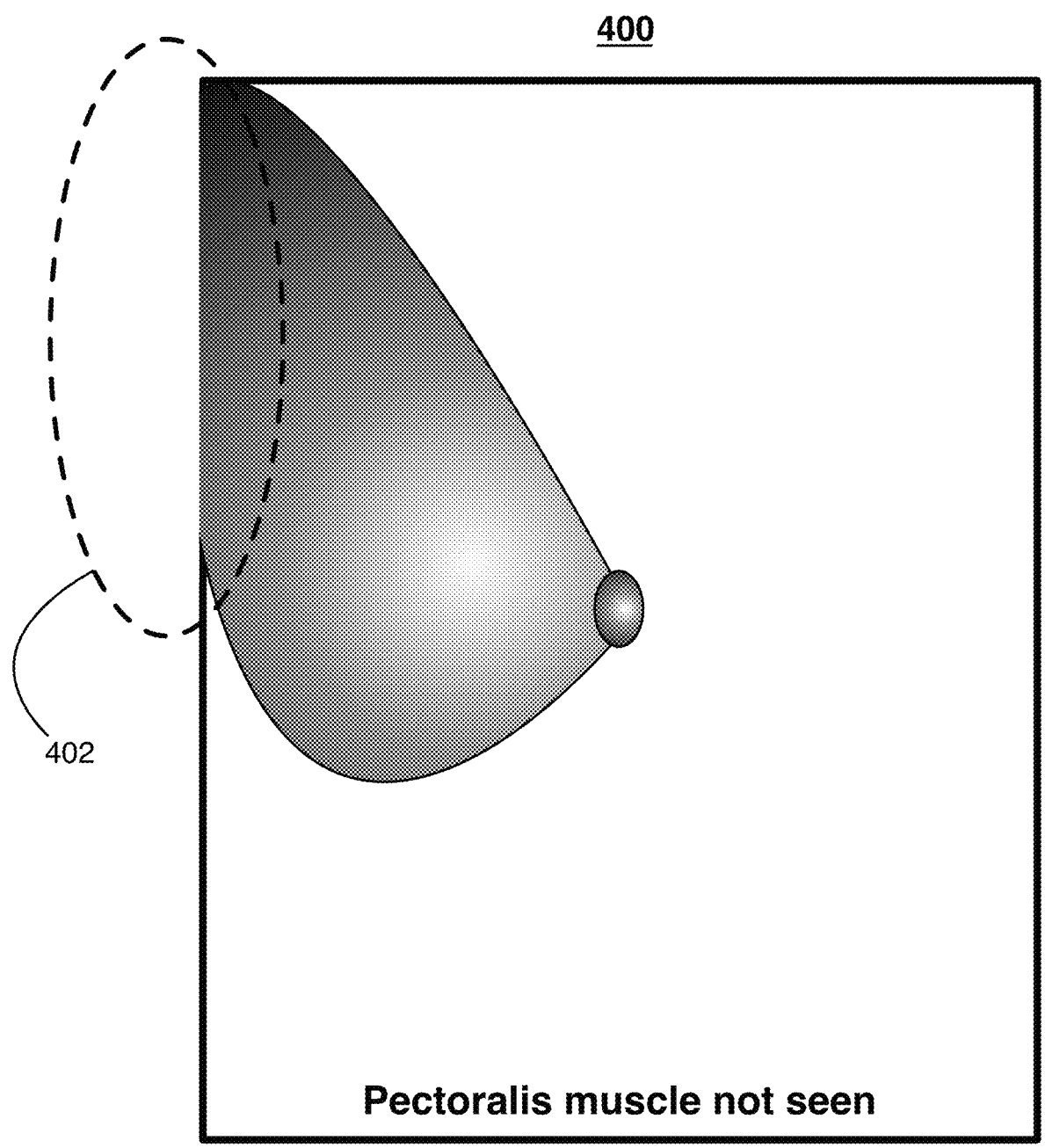
FIG. 4 illustrates a mammography image according to an embodiment.

FIG. 4 illustrates a pre-diagnostic mammography image 400 according to an embodiment. As illustrated within pre-diagnostic mammography image 400, a position analysis module may identify region 402 as lacking a pectoralis muscle. In this example, the lack of a pectoralis muscle may indicate to a position analysis module that insufficient breast tissue is present within a pre-diagnostic image, and that the patient is therefore improperly positioned.

Figure 5:
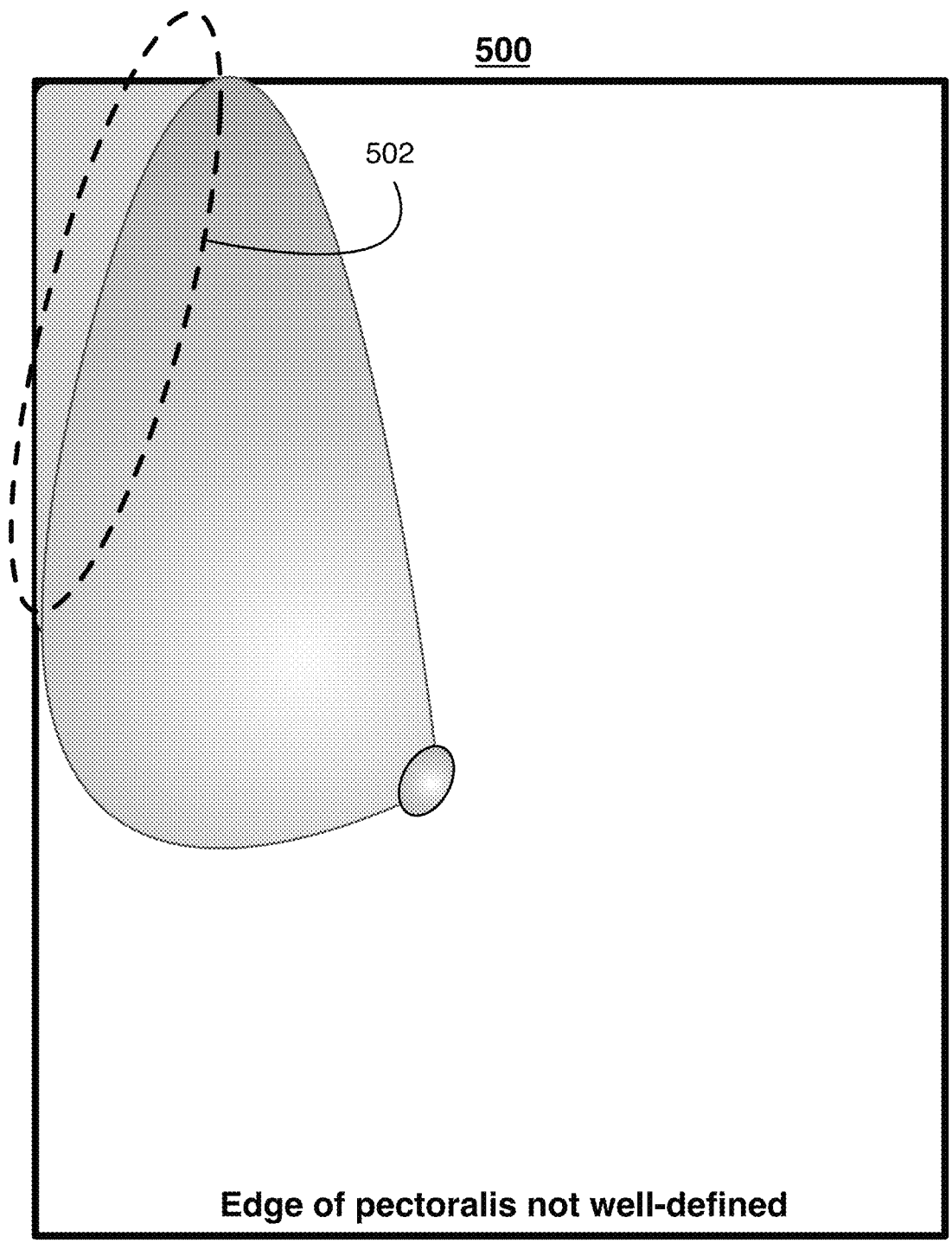
FIG. 5 illustrates a mammography image according to an embodiment.

FIG. 5 illustrates a pre-diagnostic mammography image 500 according to an embodiment. As illustrated within pre-diagnostic mammography image 500, a position analysis module may identify region 502 as lacking sufficient definition between breast tissue and the edge of the pectoralis muscle, which may indicate improper placement of a patient.

Figure 6:
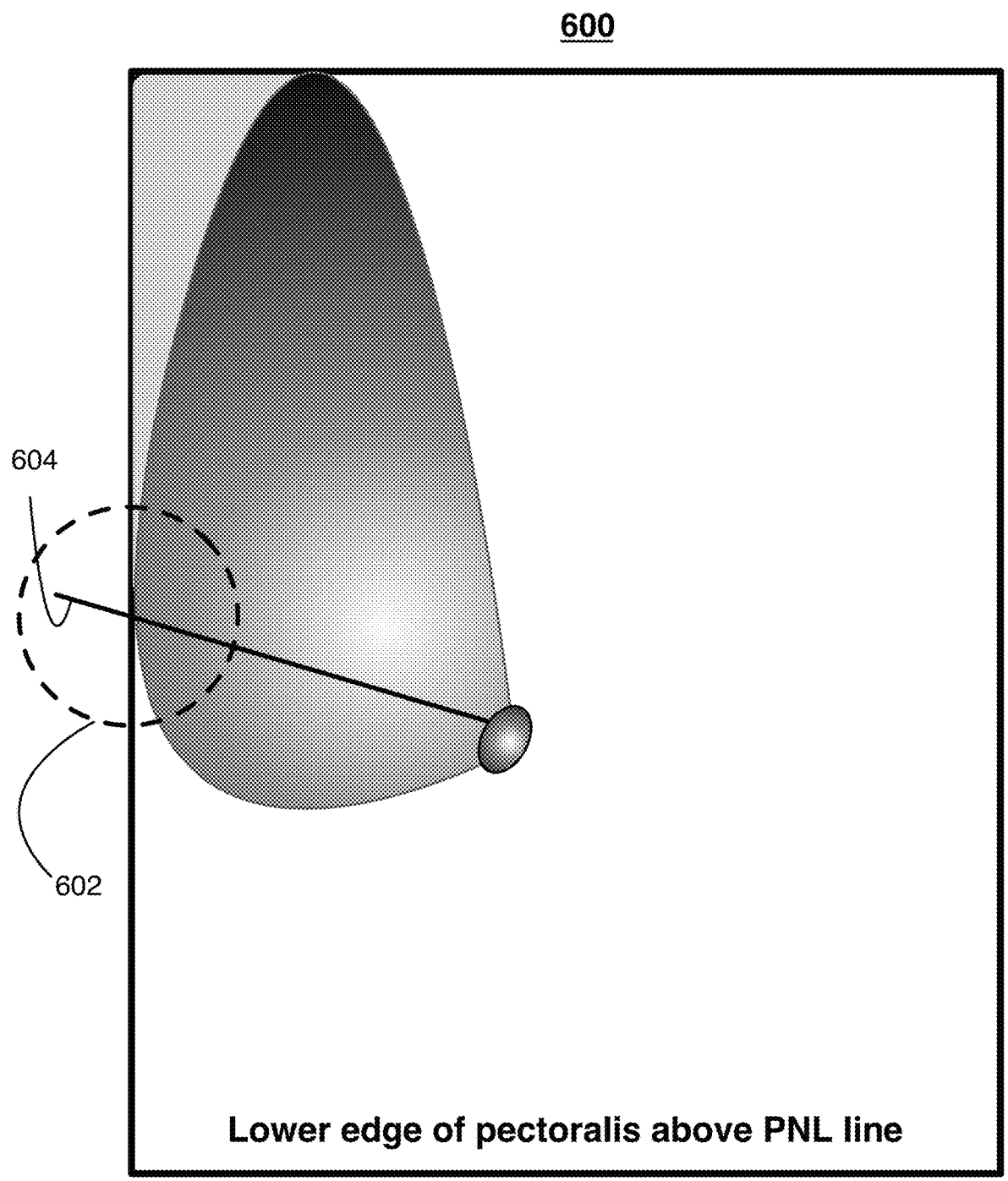
FIG. 6 illustrates a mammography image according to an embodiment.

FIG. 6 illustrates a pre-diagnostic mammography image 600 according to an embodiment. As illustrated within pre-diagnostic mammography image 600, a position analysis module may identify region 602, which includes a PNL line 604 that below the lower edge of the pectoralis muscle.

Figure 7:
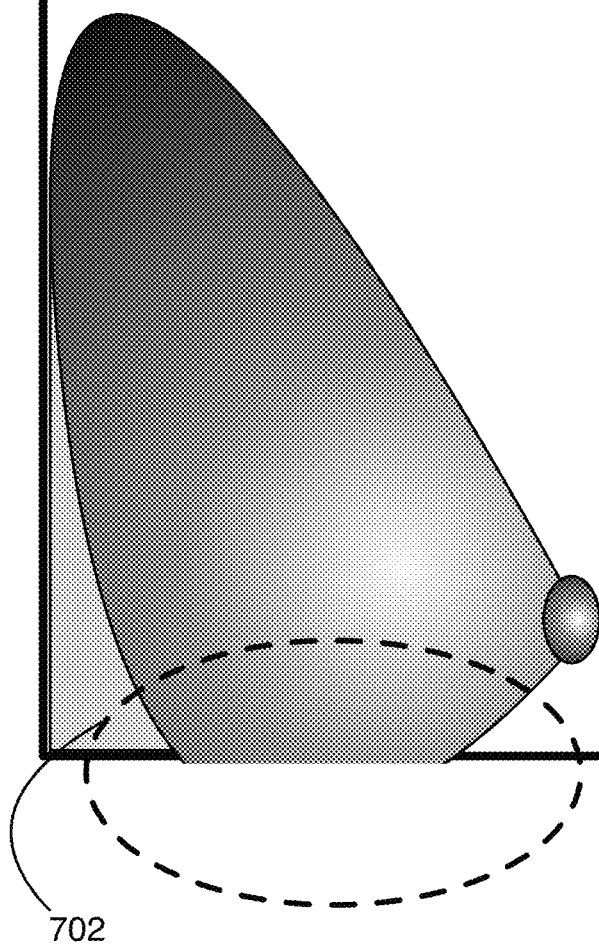
FIG. 7 illustrates a mammography image according to an embodiment.

FIG. 7 illustrates a pre-diagnostic mammography image 700 according to an embodiment. As illustrated within pre-diagnostic mammography image 700, a position analysis module may identify region 702, which may lack adequate coverage of the lower quadrant of the breast tissue, and may indicate improper patient positioning.

Figure 8:
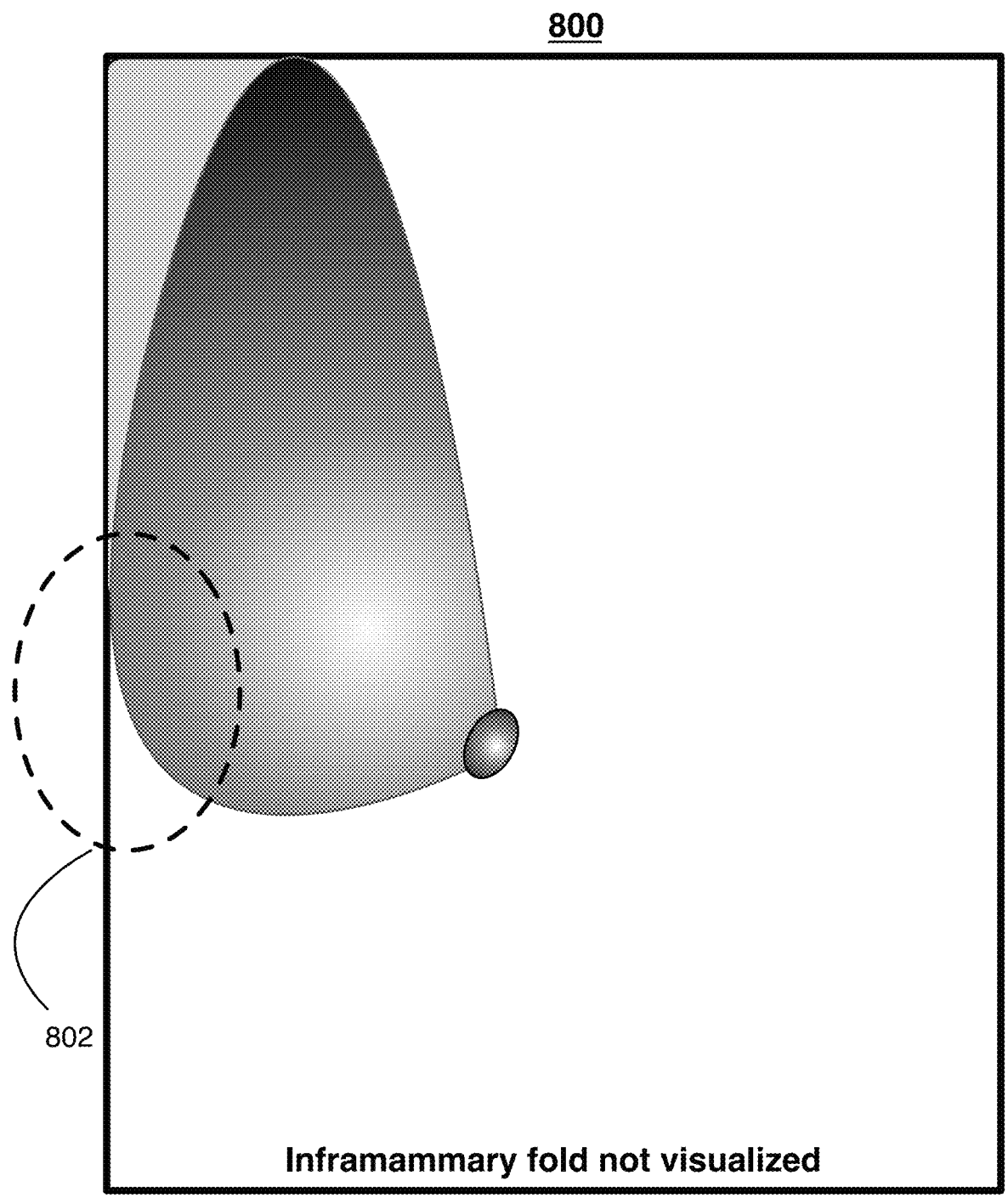
FIG. 8 illustrates a mammography image according to an embodiment.

FIG. 8 illustrates a pre-diagnostic mammography image 800 according to an embodiment. As illustrated within pre-diagnostic mammography image 800, a position analysis module may identify region 802 as lacking, or insufficiently visualizing, the inframammary fold, which may indicate improper patient positioning.

Figure 9:
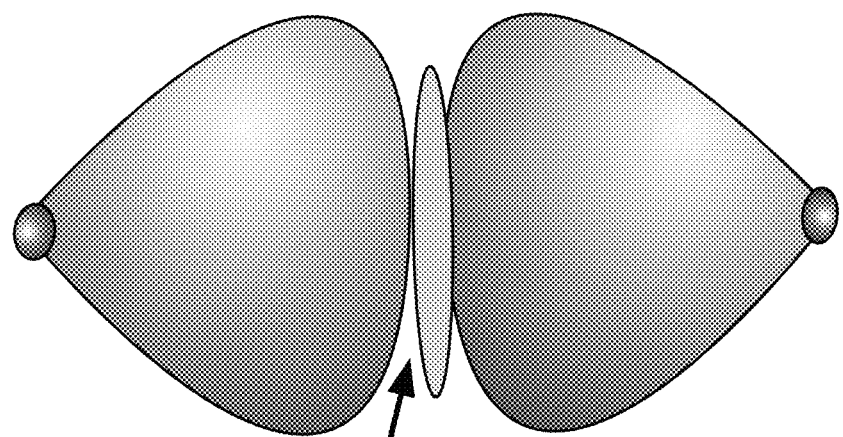
FIG. 9 illustrates a mammography image according to an embodiment.

FIG. 9 illustrates a pre-diagnostic mammography image 900 according to an embodiment. As illustrated within pre-diagnostic mammography image 900, a position analysis module may identify region 902 in a comparison between two CC views. In an embodiment, the CC views may be from the same study and may represent the right and left breasts of a patient. As illustrated by region 902, a position analysis module may identify a pectoralis in the middle of the two breasts, which may indicate all, or most (for example, an amount over a threshold), breast tissue along chest wall is included in the image, and may provide evidence of proper patient positioning.

Figure 10:
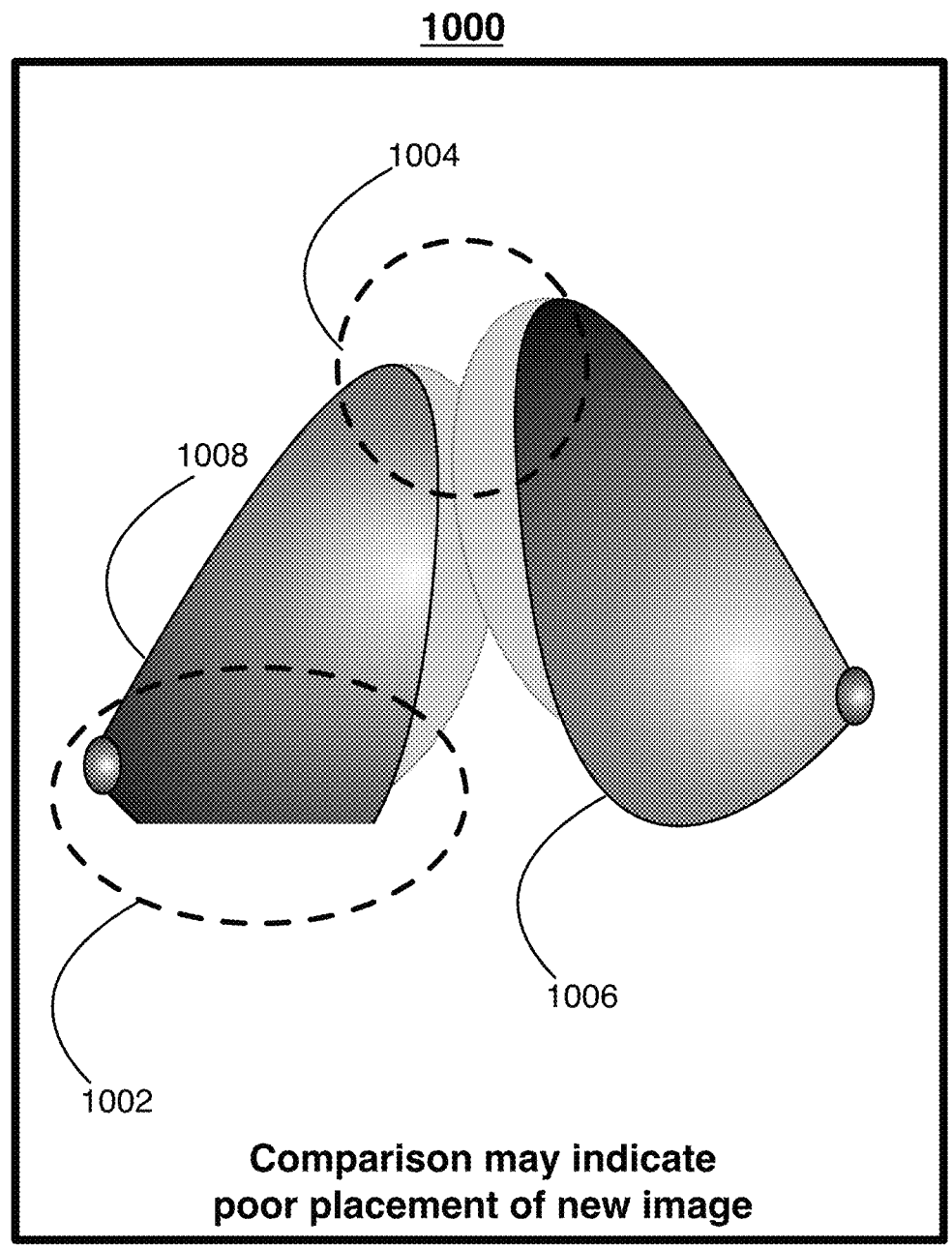
FIG. 10 illustrates a mammography image according to an embodiment.

FIG. 10 illustrates a pre-diagnostic mammography image 1000 according to an embodiment. As illustrated within pre-diagnostic mammography image 1000, a position analysis module may identify region 1002 and region 1004 in a comparison between breast 1006 and 1008. In an embodiment, pre-diagnostic images of breasts 1006 and 1008 may be from the same study. However, in other embodiments, one of the images of breasts 1006 or 1008 may be from a previous study, and may comprise a diagnostic or pre-diagnostic image. As set forth within regions 1002 and 1004, the image of breast 1008 may be misaligned with the image of breast 1006, indicating poor patient positioning.

Included herein is a set of flow charts representative of exemplary methodologies for performing novel aspects of the disclosed architecture. While, for purposes of simplicity of explanation, the one or more methodologies shown herein, for example, in the form of a flow chart or flow diagram, are shown and described as a series of acts, it is to be understood and appreciated that the methodologies are not limited by the order of acts, as some acts may, in accordance therewith, occur in a different order and/or concurrently with other acts from that shown and described herein. For example, those skilled in the art will understand and appreciate that a methodology could alternatively be represented as a series of interrelated states or events, such as in a state diagram. Moreover, not all acts illustrated in a methodology may be required for a novel implementation.

Figure 11:
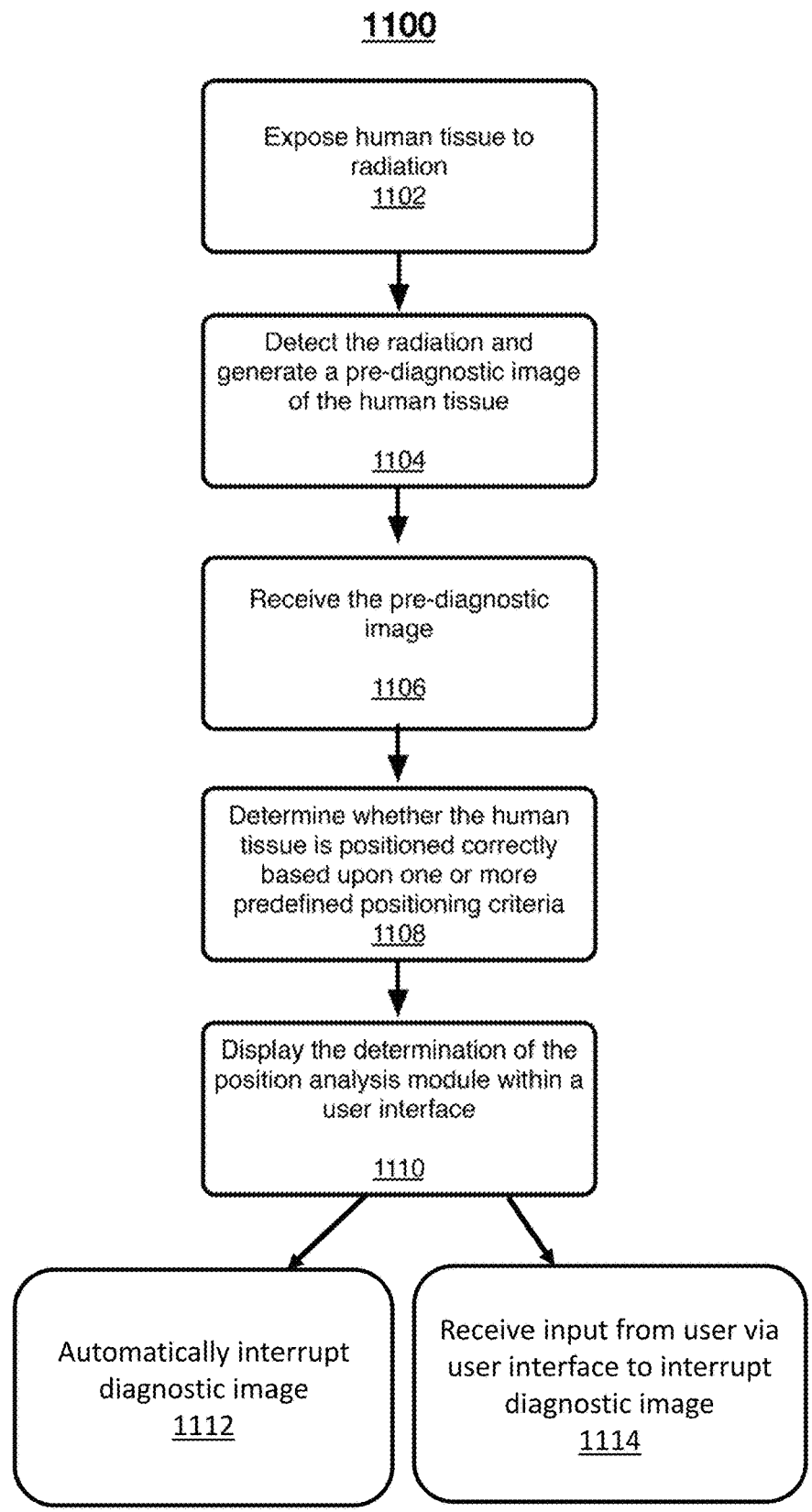
FIG. 11 illustrates a logic flow according to an embodiment.

FIG. 11 illustrates a logic flow 1100 according to an embodiment. The logic flow 1100 may be representative of some or all of the operations executed by one or more embodiments described herein, such as imaging system 100, for example. At 1102, human tissue may be exposed to radiation by an x-ray source.

At 1104, radiation may be detected by an x-ray detector and a pre-diagnostic image of the human tissue may be generated by a pre-diagnostic imaging module. The output image may be an AEC scout image. AEC scout images may be pre-diagnostic and used to measure and calibrate radiation levels within an imaging system prior to taking diagnostic images. In other words, AEC scout images may be taken prior to typical diagnostic images, be of a lower resolution than diagnostic images, and require less radiation than diagnostic images. In some embodiments, pre-diagnostic AEC scout images may contain approximately 2% of the radiation as a diagnostic image (or another amount below the amount of radiation for capturing a diagnostic image) (i.e., a pre-diagnostic dose level). While the very low radiation dosage of pre-diagnostic images is beneficial to patients, it also may significantly decrease the resolution of an image.

At 1106, the pre-diagnostic image may be received by a position analysis module. Position analysis module 114 may evaluate the received image, which may be of a low resolution when compared to a diagnostic image. Using algorithms optimized to identify anatomical landmarks within low resolution pre-diagnostic images, a position analysis module may identify one or more anatomical landmarks as discussed above.

At 1108, it may be determined whether the human tissue is positioned correctly based upon one or more predefined positioning criteria. Once identified, characteristics of detected anatomical landmarks (e.g., location, position, presence, size, relationship to other landmarks, etc.) may be compared to one or more predefined criteria from position criteria repository. Based upon the comparison, a position analysis module may make a position determination. In some embodiments, a position analysis module may make a position determination based upon the relationship of a first landmark to one or more additional landmarks, and/or a comparison of a current pre-diagnostic view with a previous pre-diagnostic or diagnostic view accessible from an image database.

At 1110, the determination of the position analysis module may be stored on a non-transitory computer-readable storage medium. In an embodiment, one or more pre-diagnostic images may also be stored on the non-transitory computer-readable storage medium, or another local or remote storage medium. In this manner, the determination and/or one or more pre-diagnostic images may be referenced and used within a position analysis within the current study or a future study. In some embodiments, a user interface of a display device may display the determination of the position analysis module. A display device may be configured to receive and display a determination of patient positioning from a position analysis module. For example, a practitioner may be notified via the user interface of a display device that a patient is properly or improperly positioned. In various embodiments, a position analysis module may indicate to a practitioner, based upon a position determination, suggested movements for a patient to obtain proper positioning prior to a diagnostic image.

At 1112, based on the determination of the position analysis module that the patient is improperly positioned, the imaging module is automatically interrupted before activating and taking the full exposure diagnostic image and exposing the patient to radiation from the x-ray source. Alternatively, at 1114, based on the determination of the position analysis module that the patient is improperly positioned, the display device displays a selection for the practitioner to interrupt the diagnostic image. The input is received and in response the imaging module may be interrupted prior to activating and exposing the patient to radiation from the x-ray source.

FIGS. 12A and 12B illustrate a comparison between diagnostic (FIG. 12A) and pre-diagnostic (FIG. 12B) images of a breast. As can be seen within FIG. 12A, the diagnostic image includes greater detail, and a clear view of the breast. As can be seen within FIG. 12B, the pre-diagnostic image includes significantly less detail, due in part, to a significantly lower level of radiation used to generate the image. A significant reduction in radiation may lead to pre-diagnostic images with increased noise and reduced contrast when compared to diagnostic images, which can be seen in the comparison of FIGS. 12A and 12B.

Figure 13:
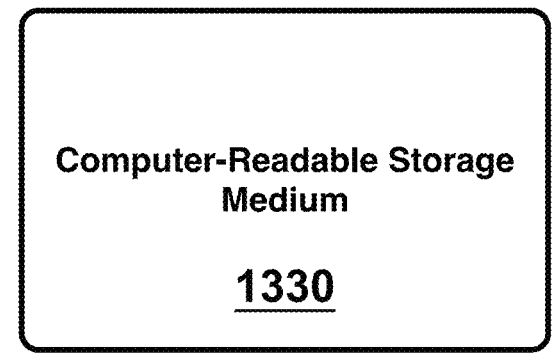
FIG. 13 illustrates an article of manufacture according to an embodiment.

FIG. 13 illustrates an article of manufacture according to an embodiment. Storage medium 1300 may comprise any computer-readable storage medium or machine-readable storage medium, such as an optical, magnetic or semiconductor storage medium. In some embodiments, storage medium 1300 may comprise a non-transitory storage medium. In various embodiments, storage medium 1300 may comprise an article of manufacture. In some embodiments, storage medium 1300 may store computer-executable instructions, such as computer-executable instructions to implement logic flow 1100, for example. Examples of a computer-readable storage medium or machine-readable storage medium may include any tangible media capable of storing electronic data, including volatile memory or non-volatile memory, removable or non-removable memory, erasable or non-erasable memory, writeable or re-writeable memory, and so forth. Examples of computer-executable instructions may include any suitable type of code, such as source code, compiled code, interpreted code, executable code, static code, dynamic code, object-oriented code, visual code, and the like. The embodiments are not limited to these examples.

Figure 14:
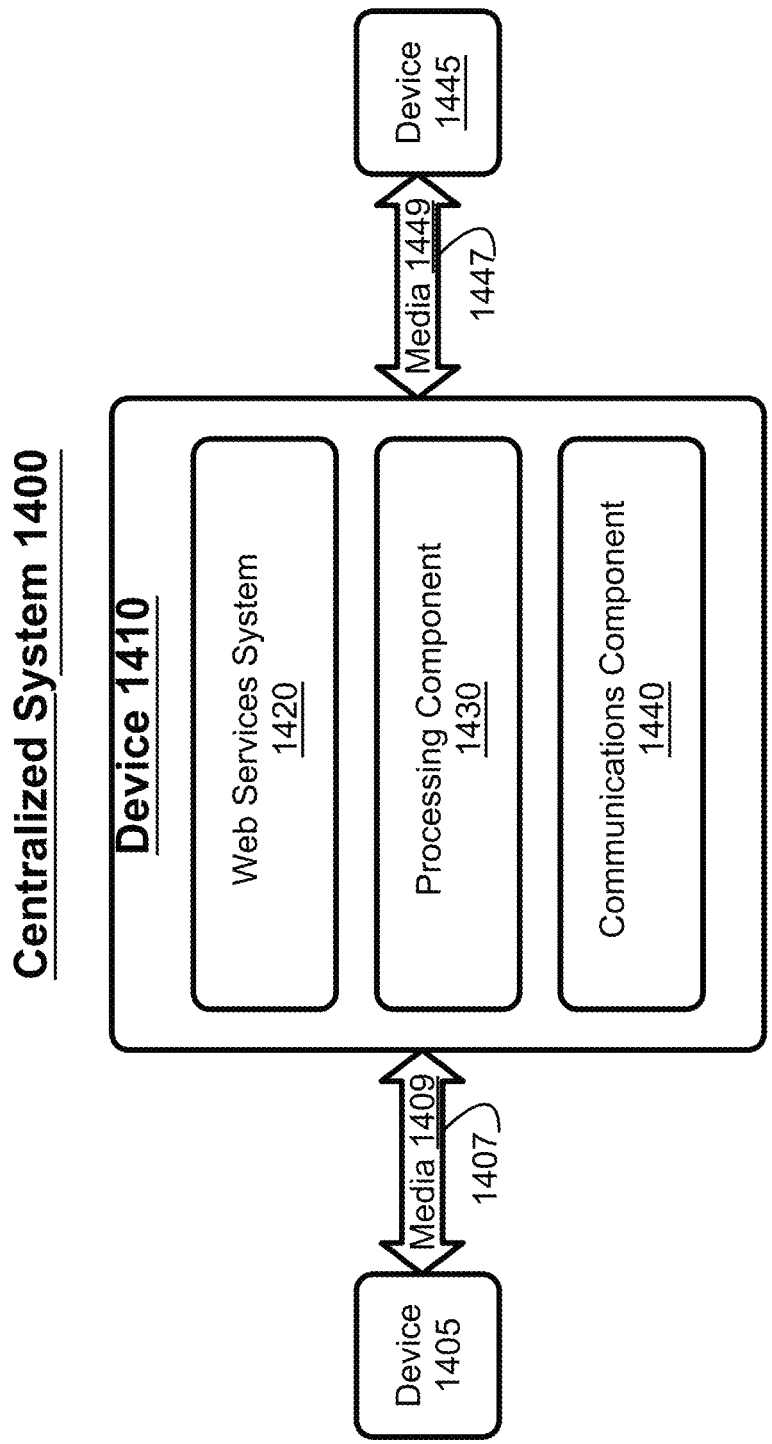
FIG. 14 illustrates an embodiment of a centralized system.

FIG. 14 illustrates a block diagram of a centralized system 1400. The centralized system 1400 may implement some or all of the structure and/or operations for the web services system 1420 in a single computing entity, such as entirely within a single device 1410.

The device 1410 may comprise any electronic device capable of receiving, processing, and sending information for the web services system 1420. Examples of an electronic device may include without limitation an imaging system, client device, a personal digital assistant (PDA), a mobile computing device, a smart phone, a cellular telephone, ebook readers, a messaging device, a computer, a personal computer (PC), a desktop computer, a laptop computer, a notebook computer, a netbook computer, a handheld computer, a tablet computer, a server, a server array or server farm, a web server, a network server, an Internet server, a work station, a network appliance, a web appliance, a distributed computing system, multiprocessor systems, processor-based systems, consumer electronics, programmable consumer electronics, game devices, television, set top box, wireless access point, base station, subscriber station, mobile subscriber center, radio network controller, router, hub, gateway, bridge, switch, machine, or combination thereof. The embodiments are not limited in this context.

The device 1410 may execute processing operations or logic for the web services system 1420 using a processing component 1430. The processing component 1430 may comprise various hardware elements, software elements, or a combination of both. Examples of hardware elements may include devices, logic devices, components, processors, microprocessors, circuits, processor circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), memory units, logic gates, registers, semiconductor device, chips, microchips, chip sets, and so forth. Examples of software elements may include software components, programs, applications, computer programs, application programs, system programs, software development programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints, as desired for a given implementation.

The device 1410 may execute communications operations or logic for the web services system 1420 using communications component 1440. The communications component 1440 may implement any well-known communications techniques and protocols, such as techniques suitable for use with packet-switched networks (e.g., public networks such as the Internet, private networks such as an enterprise intranet, and so forth), circuit-switched networks (e.g., the public switched telephone network), or a combination of packet-switched networks and circuit-switched networks (with suitable gateways and translators). The communications component 1440 may include various types of standard communication elements, such as one or more communications interfaces, network interfaces, network interface cards (NIC), radios, wireless transmitters/receivers (transceivers), wired and/or wireless communication media, physical connectors, and so forth. By way of example, and not limitation, communication media 1409, 1449 include wired communications media and wireless communications media. Examples of wired communications media may include a wire, cable, metal leads, printed circuit boards (PCB), backplanes, switch fabrics, semiconductor material, twisted-pair wire, co-axial cable, fiber optics, a propagated signal, and so forth. Examples of wireless communications media may include acoustic, radio-frequency (RF) spectrum, infrared and other wireless media.

The device 1410 may communicate with other devices 1405, 1445 over a communications media 1409, 1449, respectively, using communications signals 1407, 1447, respectively, via the communications component 1440. The devices 1405, 1445, may be internal or external to the device 1410 as desired for a given implementation.

For example, device 1405 may correspond to a client device such as a phone used by a user. Signals 1407 sent over media 1409 may therefore comprise communication between the phone and the web services system 1420 in which the phone transmits a request and receives a web page or other data in response.

Device 1445 may correspond to a second user device used by a different user from the first user, described above. In one embodiment, device 1445 may submit information to the web services system 1420 using signals 1447 sent over media 1449 to construct an invitation to the first user to join the services offered by web services system 1420. For example, if web services system 1420 comprises a social networking service, the information sent as signals 1447 may include a name and contact information for the first user, the contact information including phone number or other information used later by the web services system 1420 to recognize an incoming request from the user. In other embodiments, device 1445 may correspond to a device used by a different user that is a friend of the first user on a social networking service, the signals 1447 including status information, news, images, contact information, or other social-networking information that is eventually transmitted to device 1405 for viewing by the first user as part of the social networking functionality of the web services system 1420.

Figure 15:
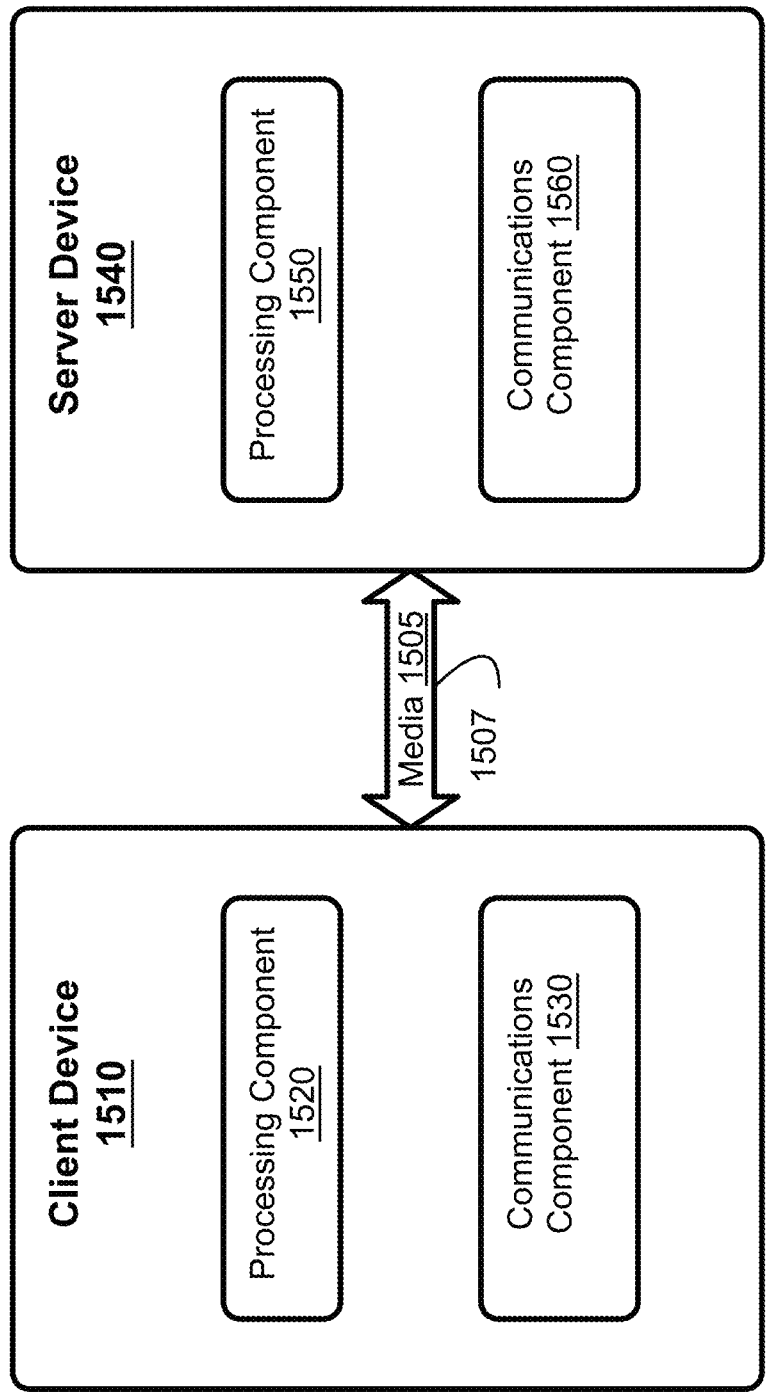
FIG. 15 illustrates an embodiment of a distributed system.

FIG. 15 illustrates a block diagram of a distributed system 1500. The distributed system 1500 may distribute portions of the structure and/or operations for the disclosed embodiments across multiple computing entities. Examples of distributed system 1500 may include without limitation a client-server architecture, a 3-tier architecture, an N-tier architecture, a tightly-coupled or clustered architecture, a peer-to-peer architecture, a master-slave architecture, a shared database architecture, and other types of distributed systems. The embodiments are not limited in this context.

The distributed system 1500 may comprise a client device 1510 and a server device 1540. In general, the client device 1510 and the server device 1540 may be the same or similar to the client device 1310 as described with reference to FIG. 14. For instance, the client system 1510 and the server system 1540 may each comprise a processing component 1520, 1550 and a communications component 1530, 1560 which are the same or similar to the processing component 1330 and the communications component 1340, respectively, as described with reference to FIG. 14. In another example, the devices 1510, 1540 may communicate over a communications media 1505 using communications signals 1507 via the communications components 1530, 1560.

The client device 1510 may comprise or employ one or more client programs that operate to perform various methodologies in accordance with the described embodiments. In one embodiment, for example, the client device 1510 may implement some steps described with respect to FIG. 11.

The server device 1540 may comprise or employ one or more server programs that operate to perform various methodologies in accordance with the described embodiments. In one embodiment, for example, the server device 1540 may implement some steps described with respect to FIG. 11.

Figure 16:
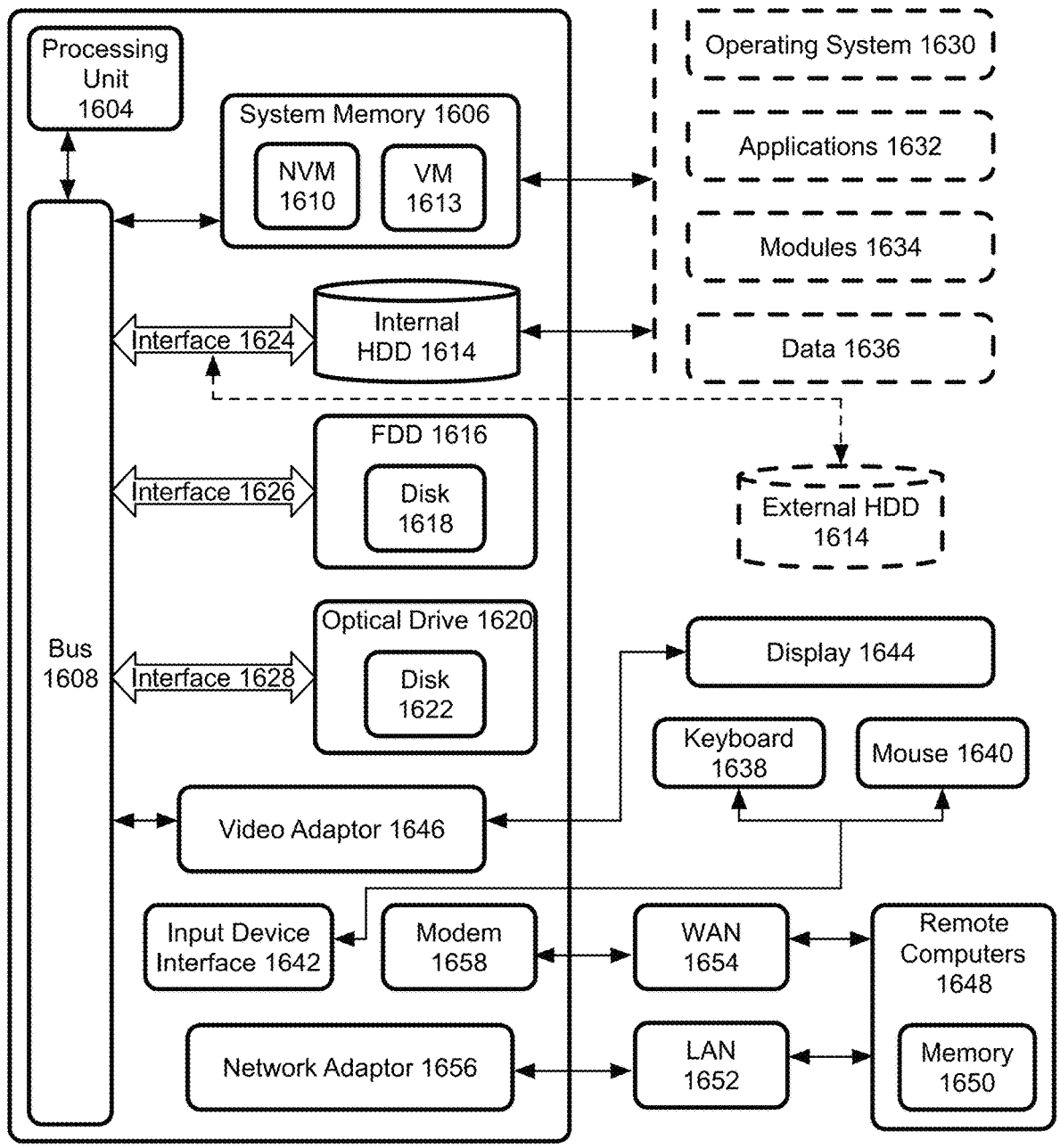
FIG. 16 illustrates an embodiment of a computing architecture.

FIG. 16 illustrates an embodiment of an exemplary computing architecture 1600 suitable for implementing various embodiments as previously described. In one embodiment, the computing architecture 1600 may comprise or be implemented as part of an electronic device. Examples of an electronic device may include those described herein. The embodiments are not limited in this context.

As used in this application, the terms "system" and "component" are intended to refer to a computer-related entity, either hardware, a combination of hardware and software, software, or software in execution, examples of which are provided by the exemplary computing architecture 1600. For example, a component can be, but is not limited to being, a process running on a processor, a processor, a hard disk drive, multiple storage drives (of optical and/or magnetic storage medium), an object, an executable, a thread of execution, a program, and/or a computer. By way of illustration, both an application running on a server and the server can be a component. One or more components can reside within a process and/or thread of execution, and a component can be localized on one computer and/or distributed between two or more computers. Further, components may be communicatively coupled to each other by various types of communications media to coordinate operations. The coordination may involve the uni-directional or bi-directional exchange of information. For instance, the components may communicate information in the form of signals communicated over the communications media. The information can be implemented as signals allocated to various signal lines. In such allocations, each message is a signal. Further embodiments, however, may alternatively employ data messages. Such data messages may be sent across various connections. Exemplary connections include parallel interfaces, serial interfaces, and bus interfaces.

The computing architecture 1600 includes various common computing elements, such as one or more processors, multi-core processors, co-processors, memory units, chipsets, controllers, peripherals, interfaces, oscillators, timing devices, video cards, audio cards, multimedia input/output (I/O) components, power supplies, and so forth. The embodiments, however, are not limited to implementation by the computing architecture 1600.

As shown in FIG. 16, the computing architecture 1600 comprises a processing unit 1604, a system memory 1606 and a system bus 1608. Dual microprocessors, multi-core processors, and other multi-processor architectures may also be employed as the processing unit 1604.

The system bus 1608 provides an interface for system components including, but not limited to, the system memory 1606 to the processing unit 1604. The system bus 1608 can be any of several types of bus structure that may further interconnect to a memory bus (with or without a memory controller), a peripheral bus, and a local bus using any of a variety of commercially available bus architectures. Interface adapters may connect to the system bus 1608 via a slot architecture, for example.

The computing architecture 1600 may comprise or implement various articles of manufacture. An article of manufacture may comprise a computer-readable storage medium to store logic, as described above with respect to FIG. 13.

The system memory 1606 may include various types of computer-readable storage media in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In the illustrated embodiment shown in FIG. 16, the system memory 1606 can include non-volatile memory 1610 and/or volatile memory 1613. A basic input/output system (BIOS) can be stored in the non-volatile memory 1610.

The computer 1602 may include various types of computer-readable storage media in the form of one or more lower speed memory units, including an internal (or external) hard disk drive (HDD) 1614, a magnetic floppy disk drive (FDD) 1616 to read from or write to a removable magnetic disk 1618, and an optical disk drive 1620 to read from or write to a removable optical disk 1622 (e.g., a CD-ROM, DVD, or Blu-ray). The HDD 1614, FDD 1616 and optical disk drive 1620 can be connected to the system bus 1608 by a HDD interface 1624, an FDD interface 1626 and an optical drive interface 1628, respectively. The HDD interface 1624 for external drive implementations can include at least one or both of Universal Serial Bus (USB) and IEEE 1394 interface technologies.

The drives and associated computer-readable media provide volatile and/or nonvolatile storage of data, data structures, computer-executable instructions, and so forth. For example, a number of program modules can be stored in the drives and memory units 1610, 1613, including an operating system 1630, one or more application programs 1632, other program modules 1634, and program data 1636. In one embodiment, the one or more application programs 1632, other program modules 1634, and program data 1636 can include, for example, the various applications and/or components to implement the disclosed embodiments.

A user can enter commands and information into the computer 1602 through one or more wire/wireless input devices, for example, a keyboard 1638 and a pointing device, such as a mouse 1640. Other input devices may include microphones, infra-red (IR) remote controls, radio-frequency (RF) remote controls, game pads, stylus pens, card readers, dongles, finger print readers, gloves, graphics tablets, joysticks, keyboards, retina readers, touch screens (e.g., capacitive, resistive, etc.), trackballs, trackpads, sensors, styluses, and the like. These and other input devices are often connected to the processing unit 1604 through an input device interface 1642 that is coupled to the system bus 1608, but can be connected by other interfaces such as a parallel port, IEEE 1394 serial port, a game port, a USB port, an IR interface, and so forth.

A display 1644 is also connected to the system bus 1608 via an interface, such as a video adaptor 1646. The display 1644 may be internal or external to the computer 1602. In addition to the display 1644, a computer typically includes other peripheral output devices, such as speakers, printers, and so forth.

The computer 1602 may operate in a networked environment using logical connections via wire and/or wireless communications to one or more remote computers, such as a remote computer 1648. The remote computer 1648 can be a workstation, a server computer, a router, a personal computer, portable computer, microprocessor-based entertainment appliance, a peer device or other common network node, and typically includes many or all of the elements described relative to the computer 1602, although, for purposes of brevity, only a memory/storage device 1650 is illustrated. The logical connections depicted include wire/wireless connectivity to a local area network (LAN) 1652 and/or larger networks, for example, a wide area network (WAN) 1654. Such LAN and WAN networking environments are commonplace in offices and companies, and facilitate enterprise-wide computer networks, such as intranets, all of which may connect to a global communications network, for example, the Internet.

When used in a LAN networking environment, the computer 1602 is connected to the LAN 1652 through a wire and/or wireless communication network interface or adaptor 1656. The adaptor 1656 can facilitate wire and/or wireless communications to the LAN 1652, which may also include a wireless access point disposed thereon for communicating with the wireless functionality of the adaptor 1656.

When used in a WAN networking environment, the computer 1602 can include a modem 1658, or is connected to a communications server on the WAN 1654, or has other means for establishing communications over the WAN 1654, such as by way of the Internet. The modem 1658, which can be internal or external and a wire and/or wireless device, connects to the system bus 1608 via the input device interface 1642. In a networked environment, program modules depicted relative to the computer 1602, or portions thereof, can be stored in the remote memory/storage device 1650. It will be appreciated that the network connections shown are exemplary and other means of establishing a communications link between the computers can be used.

The computer 1602 is operable to communicate with wire and wireless devices or entities using the IEEE 802 family of standards, such as wireless devices operatively disposed in wireless communication (e.g., IEEE 802.11 over-the-air modulation techniques). This includes at least Wi-Fi (or Wireless Fidelity), WiMax, and Bluetooth™ wireless technologies, among others. Thus, the communication can be a predefined structure as with a conventional network or simply an ad hoc communication between at least two devices. Wi-Fi networks use radio technologies called IEEE 802.11x (a, b, g, n, etc.) to provide secure, reliable, fast wireless connectivity. A Wi-Fi network can be used to connect computers to each other, to the Internet, and to wire networks (which use IEEE 802.3-related media and functions).

Figure 17:
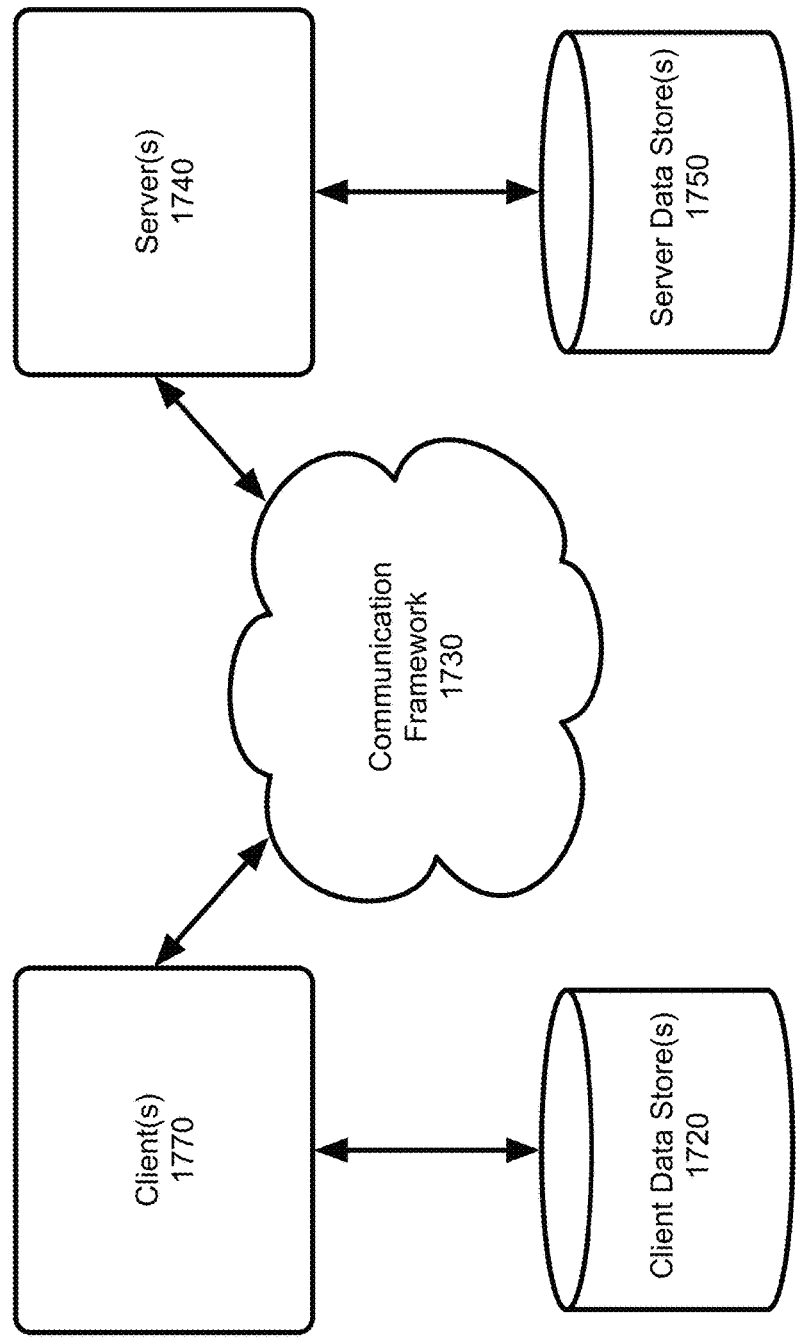
FIG. 17 illustrates an embodiment of a communications architecture.

FIG. 17 illustrates a block diagram of an exemplary communications architecture 1700 suitable for implementing various embodiments as previously described. The communications architecture 1700 includes various common communications elements, such as a transmitter, receiver, transceiver, radio, network interface, baseband processor, antenna, amplifiers, filters, power supplies, and so forth. The embodiments, however, are not limited to implementation by the communications architecture 1700.

As shown in FIG. 17, the communications architecture 1700 comprises includes one or more clients 1710 and servers 1740. The clients 1710 may implement the client device 1410, for example. The servers 1740 may implement the server device 1440, for example. The clients 1710 and the servers 1740 are operatively connected to one or more respective client data stores 1720 and server data stores 1750 that can be employed to store information local to the respective clients 1710 and servers 1740, such as cookies and/or associated contextual information.

The clients 1710 and the servers 1740 may communicate information between each other using a communication framework 1730. The communications framework 1730 may implement any well-known communications techniques and protocols. The communications framework 1730 may be implemented as a packet-switched network (e.g., public networks such as the Internet, private networks such as an enterprise intranet, and so forth), a circuit-switched network (e.g., the public switched telephone network), or a combination of a packet-switched network and a circuit-switched network (with suitable gateways and translators).

The communications framework 1730 may implement various network interfaces arranged to accept, communicate, and connect to a communications network. A network interface may be regarded as a specialized form of an input output interface. Network interfaces may employ connection protocols including without limitation direct connect, Ethernet (e.g., thick, thin, twisted pair 10/100/1000 Base T, and the like), token ring, wireless network interfaces, cellular network interfaces, IEEE 802.11a-x network interfaces, IEEE 802.17 network interfaces, IEEE 802.20 network interfaces, and the like. Further, multiple network interfaces may be used to engage with various communications network types. For example, multiple network interfaces may be employed to allow for the communication over broadcast, multicast, and unicast networks. Should processing requirements dictate a greater amount speed and capacity, distributed network controller architectures may similarly be employed to pool, load balance, and otherwise increase the communicative bandwidth required by clients 1710 and the servers 1740. A communications network may be any one and the combination of wired and/or wireless networks including without limitation a direct interconnection, a secured custom connection, a private network (e.g., an enterprise intranet), a public network (e.g., the Internet), a Personal Area Network (PAN), a Local Area Network (LAN), a Metropolitan Area Network (MAN), an Operating Missions as Nodes on the Internet (OMNI), a Wide Area Network (WAN), a wireless network, a cellular network, and other communications networks.

Some embodiments may be described using the expression "one embodiment" or "an embodiment" along with their derivatives. These terms mean that a particular feature, structure, or characteristic described in connection with the embodiment is included in at least one embodiment. The appearances of the phrase "in one embodiment" in various places in the specification are not necessarily all referring to the same embodiment. Further, some embodiments may be described using the expression "coupled" and "connected" along with their derivatives. These terms are not necessarily intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

With general reference to notations and nomenclature used herein, the detailed descriptions herein may be presented in terms of program procedures executed on a computer or network of computers. These procedural descriptions and representations are used by those skilled in the art to most effectively convey the substance of their work to others skilled in the art.

A procedure is here, and generally, conceived to be a self-consistent sequence of operations leading to a desired result. These operations are those requiring physical manipulations of physical quantities. Usually, though not necessarily, these quantities take the form of electrical, magnetic or optical signals capable of being stored, transferred, combined, compared, and otherwise manipulated. It proves convenient at times, principally for reasons of common usage, to refer to these signals as bits, values, elements, symbols, characters, terms, numbers, or the like. It should be noted, however, that all of these and similar terms are to be associated with the appropriate physical quantities and are merely convenient labels applied to those quantities.

Further, the manipulations performed are often referred to in terms, such as adding or comparing, which are commonly associated with mental operations performed by a human operator. No such capability of a human operator is necessary, or desirable in most cases, in any of the operations described herein which form part of one or more embodiments. Rather, the operations are machine operations. Useful machines for performing operations of various embodiments include general purpose digital computers or similar devices.

Various embodiments also relate to apparatus or systems for performing these operations. This apparatus may be specially constructed for the required purpose or it may comprise a general purpose computer as selectively activated or reconfigured by a computer program stored in the computer. The procedures presented herein are not inherently related to a particular computer or other apparatus. Various general purpose machines may be used with programs written in accordance with the teachings herein, or it may prove convenient to construct more specialized apparatus to perform the required method steps. The required structure for a variety of these machines will appear from the description given.

In the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment. In the appended claims, the terms "including" and "in which" are used as the plain-English equivalents of the respective terms "comprising" and "wherein," respectively. Moreover, the terms "first," "second," "third," and so forth, are used merely as labels, and are not intended to impose numerical requirements on their objects.

What has been described above includes examples of the disclosed architecture. It is, of course, not possible to describe every conceivable combination of components and/or methodologies, but one of ordinary skill in the art may recognize that many further combinations and permutations are possible.

The invention claimed is:

1. An imaging system, comprising:
   an x-ray source;
   an x-ray detector;
   a processor; and
   memory coupled to the processor, wherein the memory includes instructions that, when performed by the processor, cause the imaging system to:
   expose a human tissue to radiation emitted from the x-ray source at pre-diagnostic dose levels;
   detect the radiation at the x-ray detector;

generate a pre-diagnostic image of the human tissue based at least in part on the detected radiation;

detecting one or more anatomical landmarks; and based at least in part on the pre-diagnostic image, determine whether the human tissue is positioned correctly based upon comparing the one or more detected anatomical landmarks to one or more predefined positioning criteria.

2. The imaging system according to claim 1, wherein the pre-diagnostic image is of a lower resolution than a diagnostic image.

3. The imaging system according to claim 1, wherein the memory includes instructions that, when performed by the processor, cause the imaging system to:

generate the pre-diagnostic image of the human tissue, wherein the pre-diagnostic image is an automated exposure control (AEC) scout image.

4. The imaging system of claim 1, wherein the one or more detected anatomical landmarks are selected from a group comprising an inframammary fold, a nipple, pectoral muscles, or a chest wall.

5. The imaging system according to claim 1, wherein the one or more predefined positioning criteria include a comparison between the pre-diagnostic image and one or more of previous pre-diagnostic images or previous diagnostic images.

6. The imaging system according to claim 1, further comprising a display configured to display a user interface and a determination of whether the human tissue is positioned correctly within the user interface.

7. The imaging system according to claim 1, wherein the pre-diagnostic image is of a substantially similar resolution to a diagnostic image.

8. A computer-implemented method, comprising:

exposing a human tissue to radiation by an x-ray source;

detecting the radiation by an x-ray detector;

generating a pre-diagnostic image of the human tissue;

receiving the pre-diagnostic image at a position analysis module;

detecting one or more anatomical landmarks; and determining, by the position analysis module, whether the human tissue is positioned correctly based upon comparing the one or more detected anatomical landmarks to one or more predefined positioning criteria.

9. The computer-implemented method according to claim 8, wherein generating the pre-diagnostic image of the human tissue comprises generating the pre-diagnostic image of the human tissue at a radiation level less than a radiation level to generate a diagnostic image.

10. The computer-implemented method according to claim 8, wherein generating the pre-diagnostic image of the human tissue comprises generating an automated exposure control (AEC) scout image.

11. The computer-implemented method of claim 8, further comprising selecting the one or more detected anatomical landmarks from a group comprising an inframammary fold, a nipple, pectoral muscles, or a chest wall.

12. The computer-implemented method according to claim 8, further comprising comparing the pre-diagnostic image and one or more of previous pre-diagnostic images or previous diagnostic images, and generating the one or more predefined positioning criteria based on the comparing of the pre-diagnostic image and the one or more of previous pre-diagnostic images or the previous diagnostic images.

13. The computer-implemented method according to claim 8, further comprising displaying, by a display device, a result of the determining operation by the position analysis module.

14. The computer-implemented method according to claim 8, wherein the pre-diagnostic image is of a substantially similar resolution to a diagnostic image.

15. The computer-implemented method according to claim 8, further comprising taking automatically a diagnostic image based upon the determining operation by the position analysis module.

16. The computer-implemented method according to claim 8, further comprising stopping automatically a diagnostic image procedure based upon the determining operation by the position analysis module.

17. The computer-implemented method according to claim 8, further comprising receiving a user input based upon the determining operation by the position analysis module, and interrupting a diagnostic imaging procedure in response to the received user input.

18. An article comprising:

a non-transitory computer-readable storage medium including instructions that, when executed by a processor, cause a system to perform the computer-implemented method of claim 8.

* * * * *